United States Patent [19]
Cho et al.

[11] Patent Number: 5,665,700
[45] Date of Patent: Sep. 9, 1997

[54] PHARMACEUTICAL FORMULATIONS

[75] Inventors: Young W. Cho, Freemantle, Australia; Michael John Flynn; Thomas Smith Shepherd, both of Surrey, England

[73] Assignee: Skua Investments Limited, Douglas, Isle of Man

[21] Appl. No.: 290,293

[22] Filed: Aug. 15, 1994

Related U.S. Application Data

[63] Continuation of Ser. No. 927,394, filed as PCT/GB91/00510, Apr. 2, 1991, abandoned.

[51] Int. Cl.$^6$ .................. A61K 38/02; A61K 9/107
[52] U.S. Cl. .................. 514/2; 514/3; 514/4; 514/8; 514/12; 514/21; 514/937
[58] Field of Search .................. 514/21, 12, 8, 514/4, 3, 2, 937

[56] References Cited

U.S. PATENT DOCUMENTS

| | | | |
|---|---|---|---|
| 4,164,573 | 8/1979 | Galinsky | 424/178 |
| 4,849,227 | 7/1989 | Cho | 424/498 |

FOREIGN PATENT DOCUMENTS

| | | |
|---|---|---|
| 140085 | 5/1985 | European Pat. Off. . |
| 317120 | 5/1989 | European Pat. Off. . |
| 2581543 | 11/1986 | France . |
| 55-17328 | 2/1980 | Japan . |
| 222907 | 8/1990 | New Zealand . |
| 1180996 | 2/1970 | United Kingdom . |
| 2085729 | 5/1982 | United Kingdom . |
| 2107985 | 5/1983 | United Kingdom . |
| 87 05505 | 9/1987 | WIPO . |

*Primary Examiner*—Cecilia J. Tsang
*Assistant Examiner*—Anish Gupta
*Attorney, Agent, or Firm*—Hale and Dorr LLP

[57] ABSTRACT

A Pharmaceutical formulation comprises a biologically active material such as insulin, erythropoietin, calcitonin and growth hormone, and, associated with it, a phospholipid for forming a material which participates in the alpha-glycerol or other pathways for the formation of lecithins which are found in the intestinal epithelial cell. Biologically active protein orally administered in such a formulation are bioavailable and bioactive.

46 Claims, 10 Drawing Sheets

1

PHARMACEUTICAL FORMULATIONS

This application is a continuation of application Ser. No. 07/927,394, filed as PCT/GB91/00510, Apr. 2, 1991, now abandoned.

FIELD OF THE INVENTION

This invention relates to pharmaceutical formulations. More particularly, the invention relates to orally or rectally administrable formulations of biological active material, particularly proteinaceous materials.

BACKGROUND OF THE INVENTION

Medical practice has for many years prescribed or advised the administration of many biologically active materials for the treatment or prophylaxis of a wide variety of diseases or conditions. One of the most well known, but by no means the only, prescribed biologically active proteinaceous material is insulin, which is used for the control of diabetes.

Possibly the easiest method of taking any medication is oral ingestion. Such route of administration, which may be by means of syrup, elixir, tablets, capsules, granules, powders or any other convenient formulation, is generally simple and straightforward and is frequently the least inconvenient or unpleasant route of administration from the patient's point of view. It is therefore unfortunate, from the point of view of medical treatment and prophylaxis, that the preferred route of administration of proteinaceous medicaments and other biologically active materials involves passing the material through the stomach, which is a hostile environment for many materials, including proteins. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine.

The result, as many diabetics can testify, is that many proteinaceous medicaments have to be taken parenterally, often by subcutaneous, intramuscular or intravenous injection, with all the inconvenience, discomfort and difficulties of patient compliance that that entails.

This is not an isolated problem, as diseases needing control by the administration of proteinaceous material can be very widespread. Diabetes mellitus, for example, claims a large number of sufferers in many countries of the world. Partly because of the large number of patients suffering from diabetes of one form or another, there is a need to develop oral formulations of insulin which are somehow protected against the hostile environment of the stomach. Although various prior attempts at developing such formulations have been made, the applicants are not aware of any prior composition that has to date been commercialised to any appreciable degree. Prior proposals of which the applicants are aware are as follows.

WO-A-8701035 relates to parenterally administrable formulations of fat-soluble drugs and vitamins; the formulations comprise 'pseudomicelles'.

WO-A-8705505 discloses orally ingestible compositions of insulin coated onto solid particles from an aqueous preparation; the insulin-coated particles are themselves then coated with lipid.

U.S. Pat. No. 4,849,405 discloses orally ingestible compositions of insulin; the compositions are described as being two-phase preparations, and it appears that both phases are aqueous, with the phases effectively being kept separate by a coacervate system.

EP-A-0140085 discloses drug-containing lipid vesicle preparations.

Shichiri et al (*Acta diabet. lat.* 15 175–183 (1978)) disclose water-in-oil-in-water insulin micelles.

U.S. Pat. No. 4,784,845 and U.S. Pat. No. 4,816,247 disclose emulsion compositions for the parenteral administration of hydrophobic drugs.

JP-A-55017328 discloses water-in-oil-in-water emulsions containing insulin, for oral ingestion.

EP-A-0366277, published on 2nd May 1990, relates to improved pharmaceutical formulations that can be delivered orally or rectally. More specifically, EP-A-0366277 teaches a pharmaceutical formulation comprising a microemulsion having a hydrophilic phase and a hydrophobic phase, wherein (A) the hydrophilic phase is dispersed in the hydrophobic phase, (B) the hydrophilic phase comprises a biologically active material and (C) the hydrophobic phase contains chylomicra or material from which chylomicra are formed in vivo. The hydrophilic phase can contain a physiologically compatible solvent for the biologically active material, such as water. It is suggested that the biologically active substance, when administered in association with chylomicra or the constituents of chylomicra, is targeted to the villae and microvillae of the intestinal wall, from where it is secreted into the lacteals and intestinal lymph and then drained into the thoracic duct and, ultimately, the circulating bloodstream.

As is known, chylomicra comprise a lipid/cholesteol core or matrix, surrounded by a membrane comprising a phospholipid monolayer which is studded with proteins (Redgrave in *Gastrointestinal Physiology* IV, International Review of Physiology, Volume 28, 103–130, Young, J. A., Ed., University Park Press, Baltimore, 1983). It can thus be seen that the prior European patent application provides the biologically active material in the hyrophobic core.

SUMMARY OF THE INVENTION

This invention relates to a different approach to solving the problem of orally (or rectally) administering biologically active compounds, particularly proteins. It has been discovered that proteinaceous compounds, including but not being limited to insulin (whether bovine, porcine, human or other), growth hormone (whether human or other), calcitonin (whether salmon or other), erythropoietin (whether human or other) can be orally delivered in association with one or more phospholipids or other compounds involved in the formation of lecithin ("a lecithin precursor"). The association may be referred to as a "phospholipo-protein" (such as "phospholipo- insulin"), when the biologically active compound is proteinaceous.

DETAILED DESCRIPTION OF THE INVENTION

Figure 1:
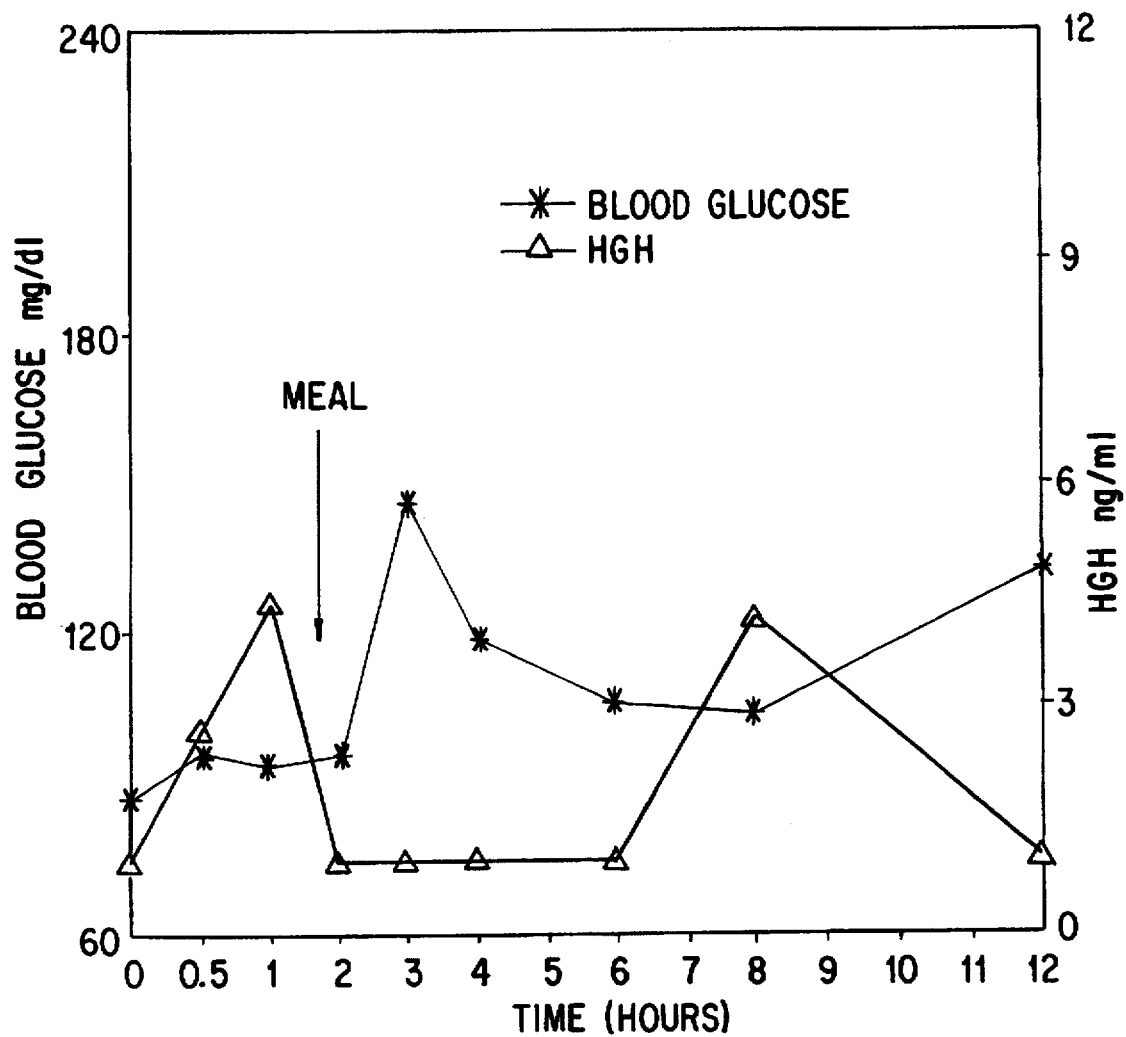
FIG. 1 shows for individual subject JBL the bioavailability measured as changes induced by oral r-hGH on blood glucose levels over time of orally administered phospholipid recombinant human growth hormone complex formulation (7 ml) of the invention.
Figure 2:
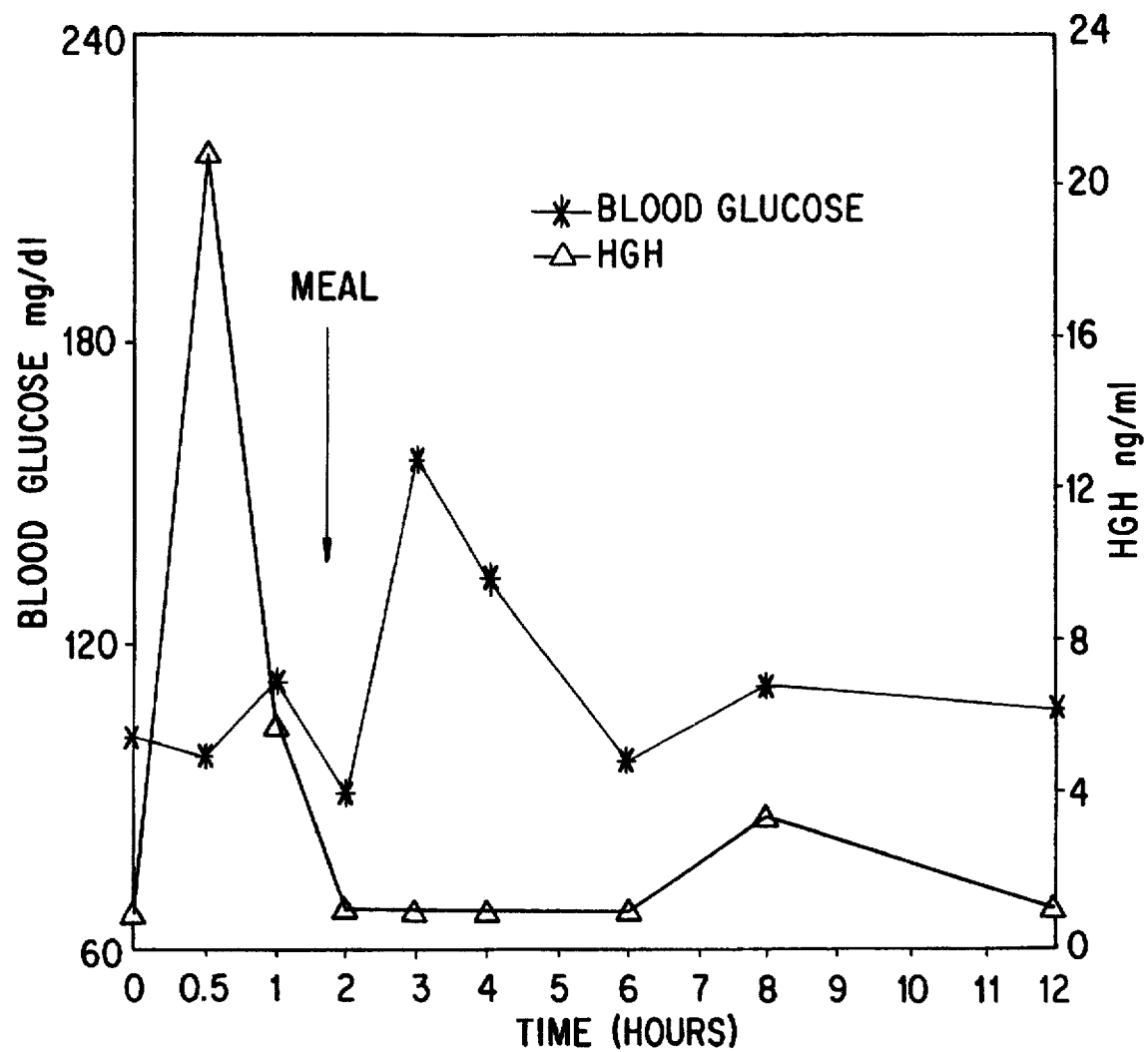
FIG. 2 shows for individual subject PJG the bioavailability measured as changes induced by oral r-hGH on blood glucose levels over time of orally administered phospholipid recombinant human growth hormone complex formulation (7 ml) of the invention.
Figure 3:
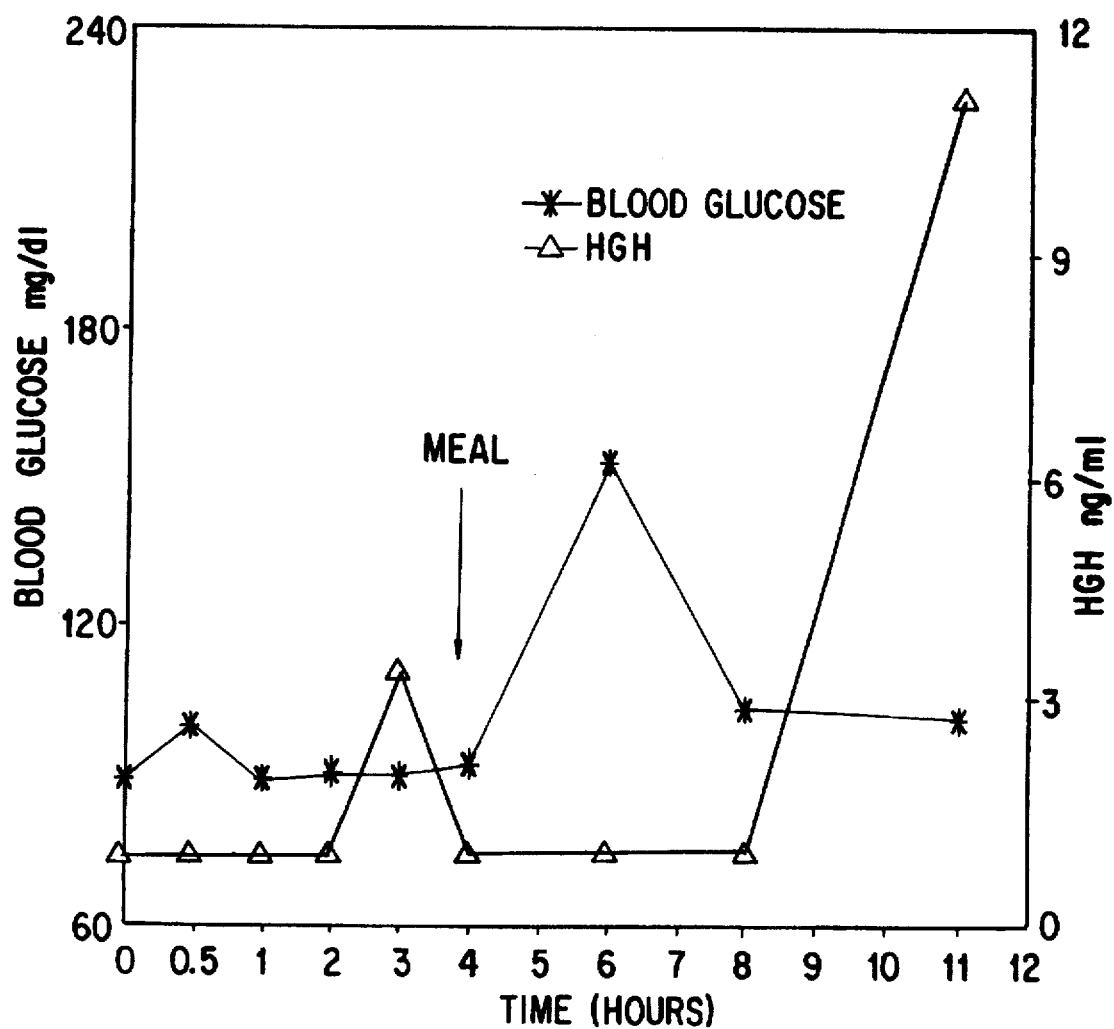
FIG. 3 shows for individual subject NMH the bioavailability measured as changes induced by oral r-hGH on blood glucose levels over time of orally administered phospholipid recombinant human growth hormone complex formulation (15 ml) of the invention.
Figure 4:
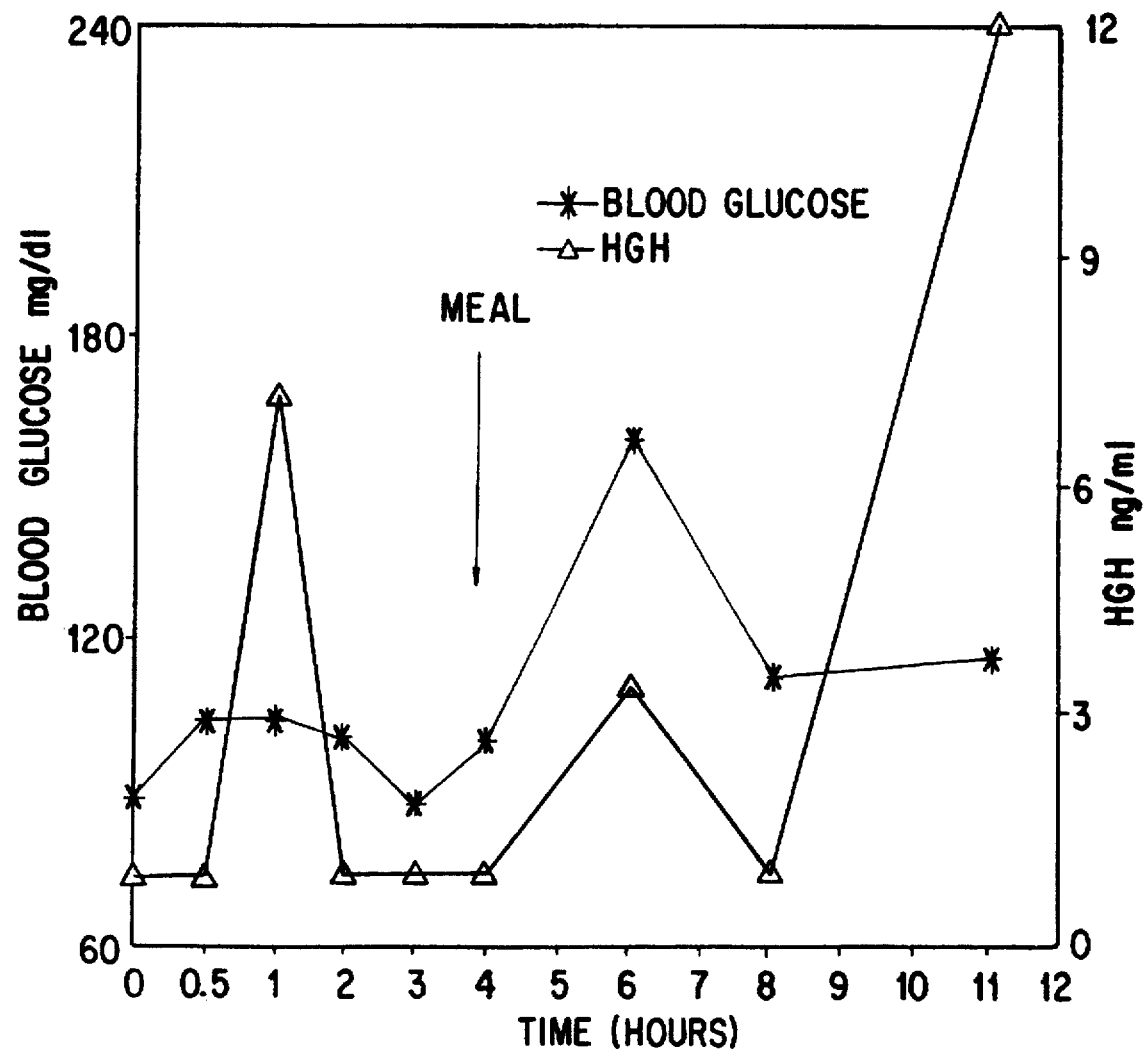
FIG. 4 shows for individual subject CSB the bioavailability measured as changes induced by oral r-hGH on blood glucose levels over time of orally administered phospholipid recombinant human growth hormone complex formulation (15 ml) of the invention.
Figure 5:
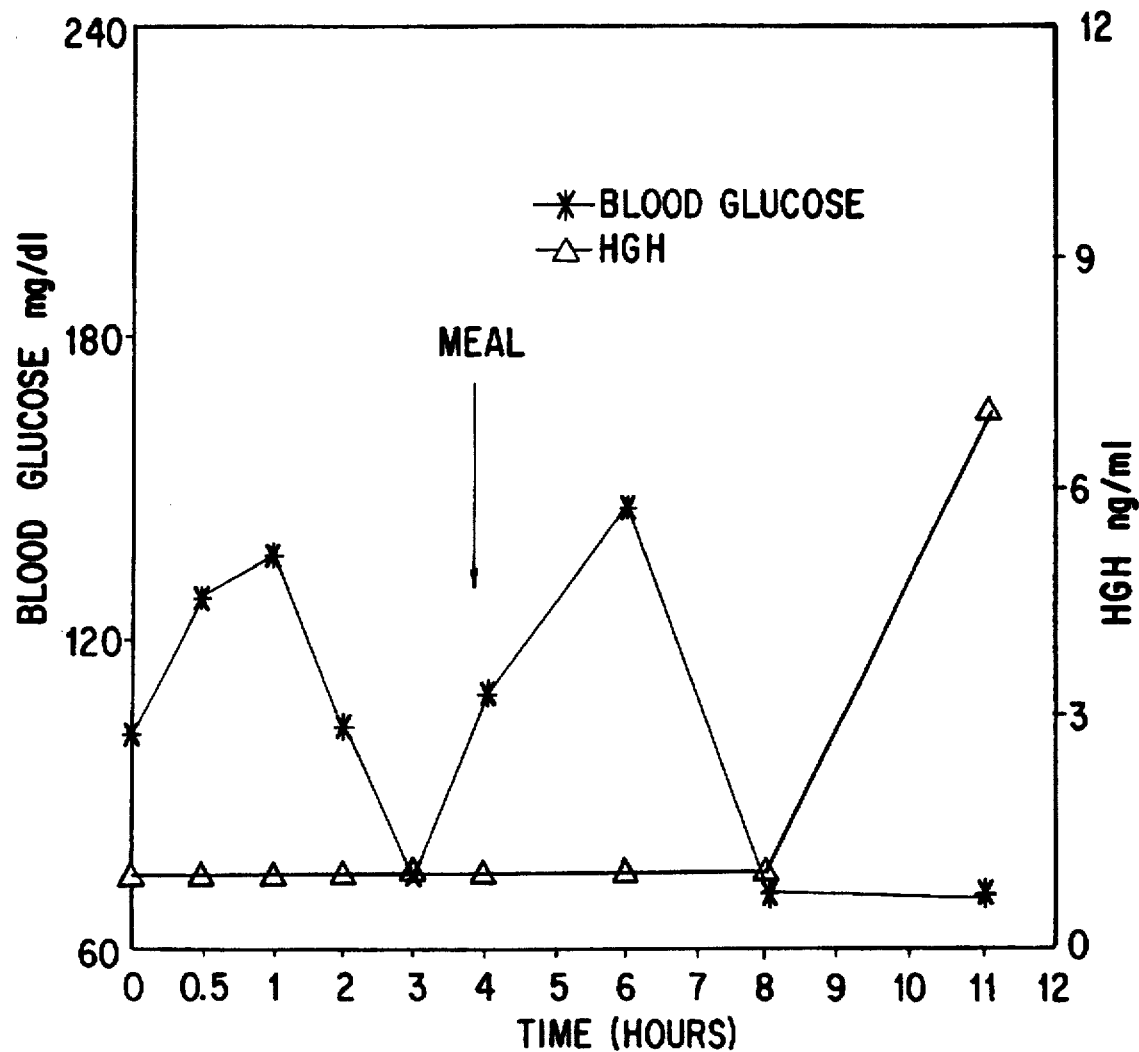
FIG. 5 shows for individual subject KKN the bioavailability measured as changes induced by oral r-hGH on blood glucose levels over time of orally administered phospholipid recombinant human growth hormone complex formulation (30 ml) of the invention.
Figure 6:
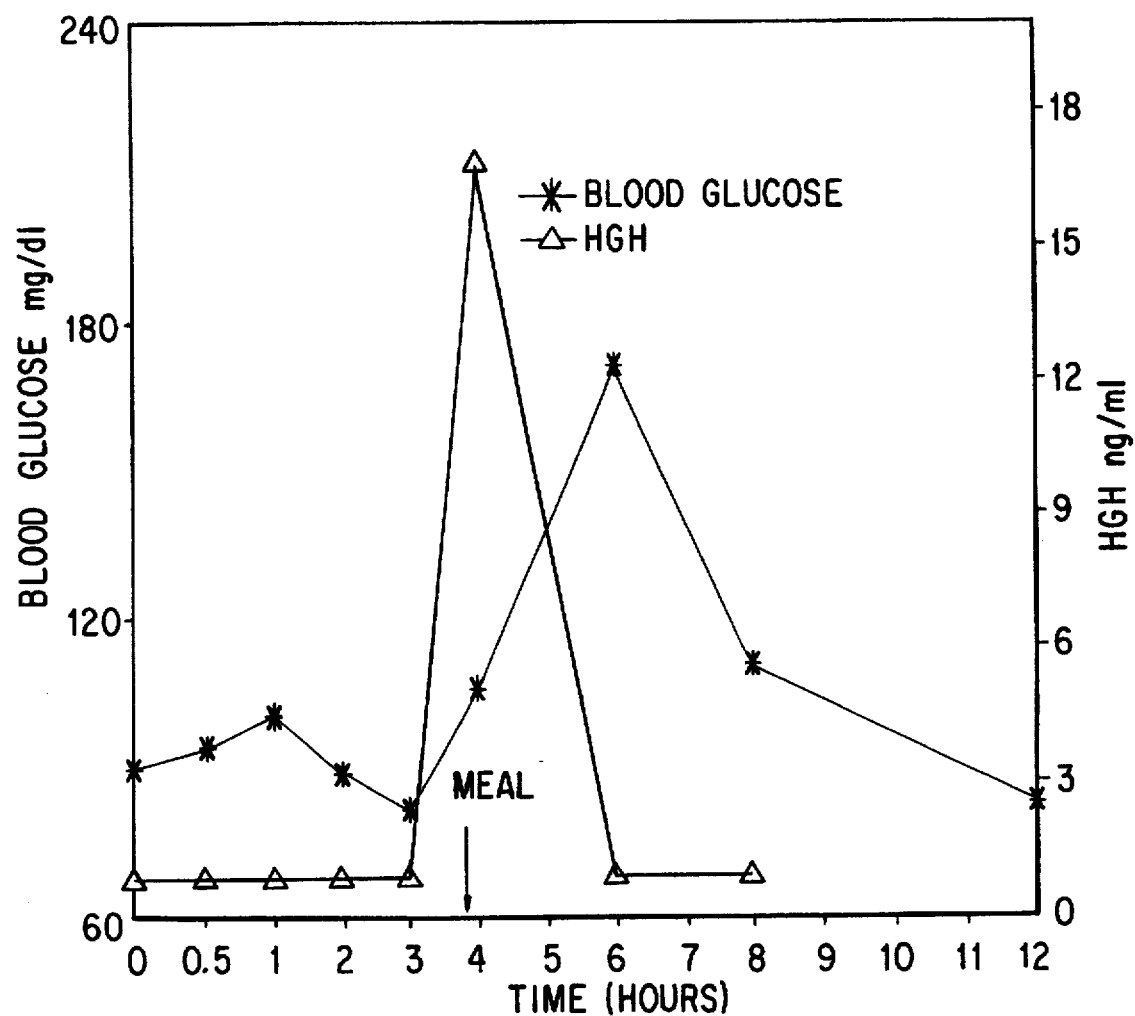
FIG. 6 shows for individual subject CSK the bioavailability measured as changes induced by oral r-hGH on blood glucose levels over time of orally administered phospholipid recombinant human growth hormone complex formulation (30 ml) of the invention.
Figure 7:
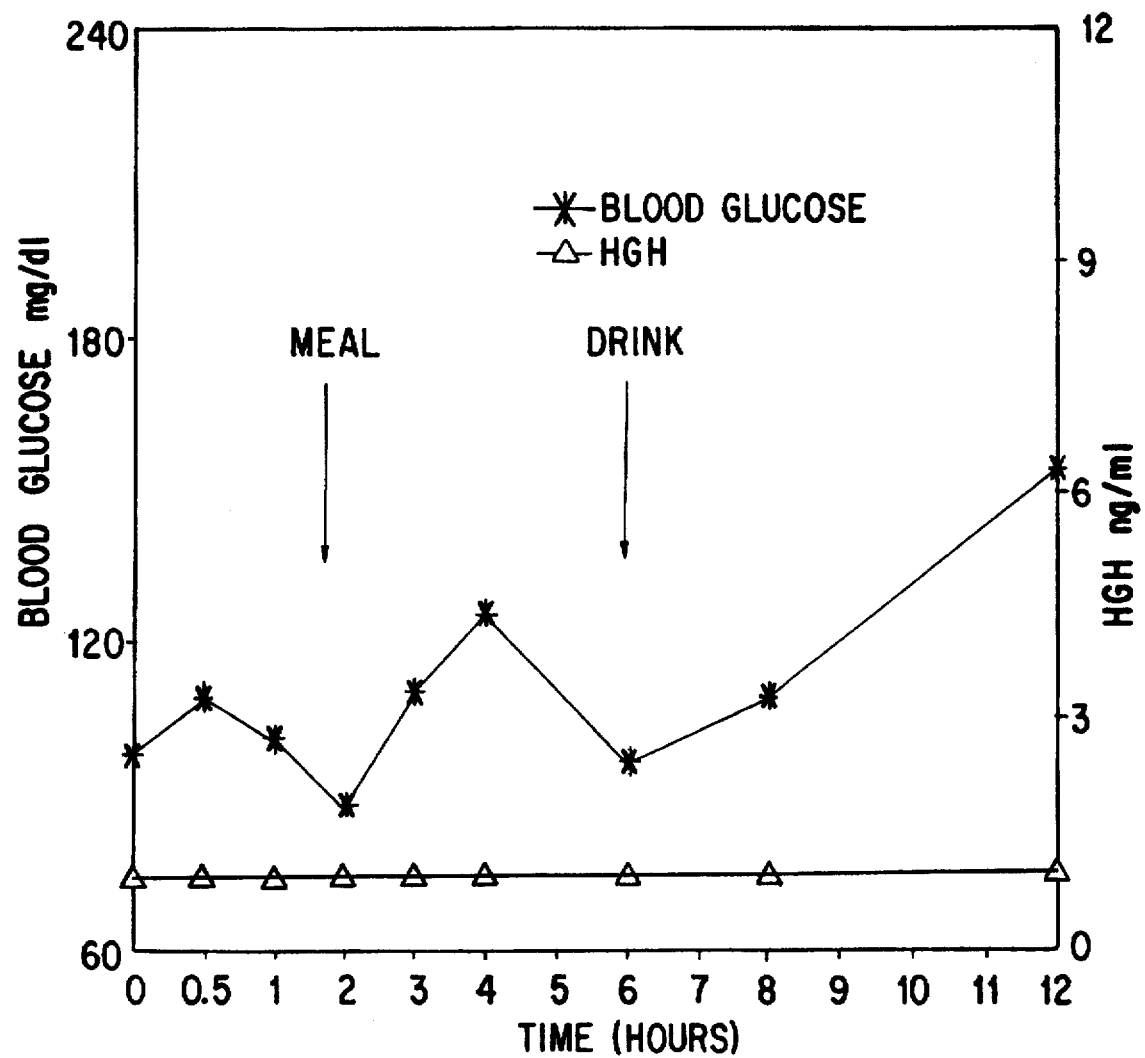
FIG. 7 shows for individual subject CYG the bioavailability over time of the control; orally administered recombinant human growth hormone.
Figure 8:
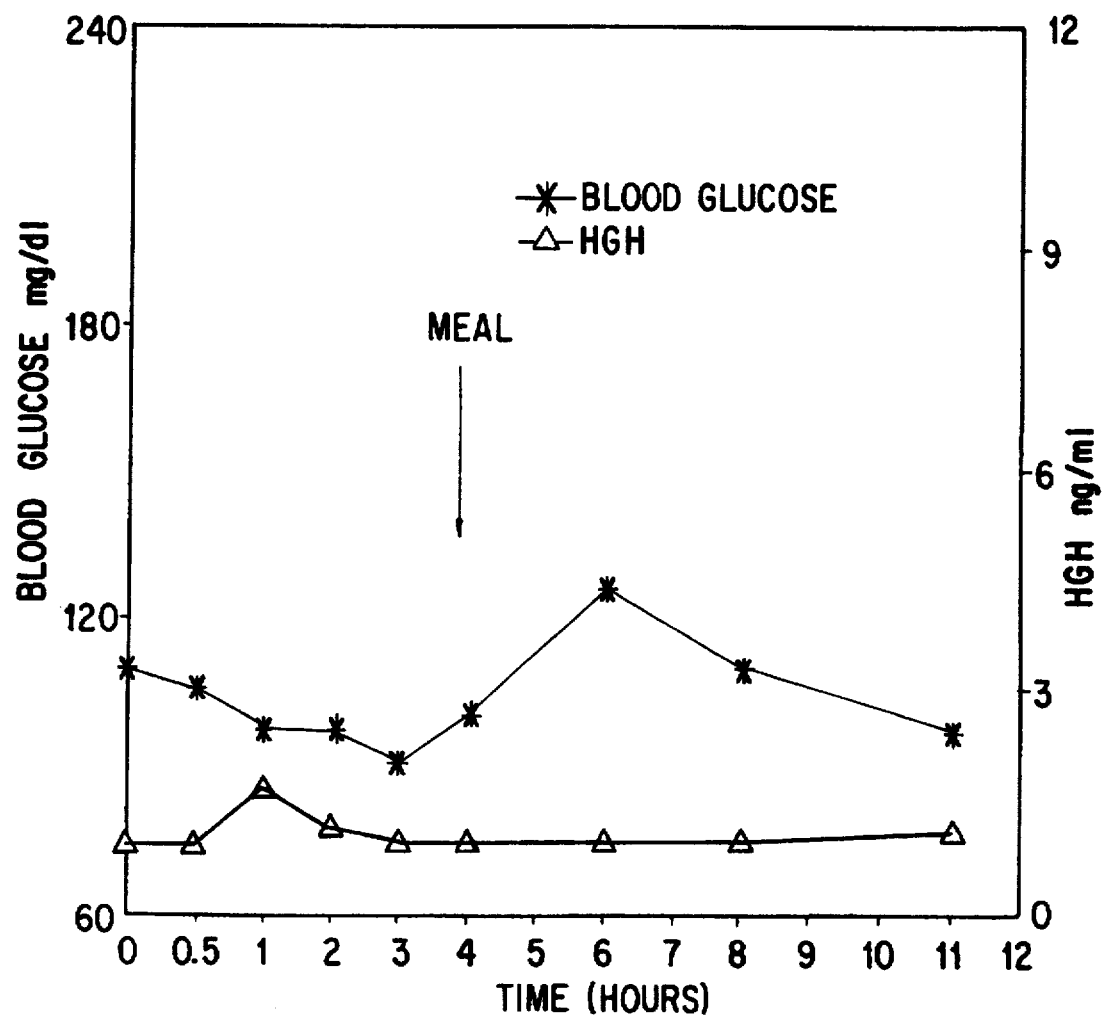
FIG. 8 shows for individual subject KJH the bioavailability over time of the control; orally administered human growth hormone.
Figure 9:
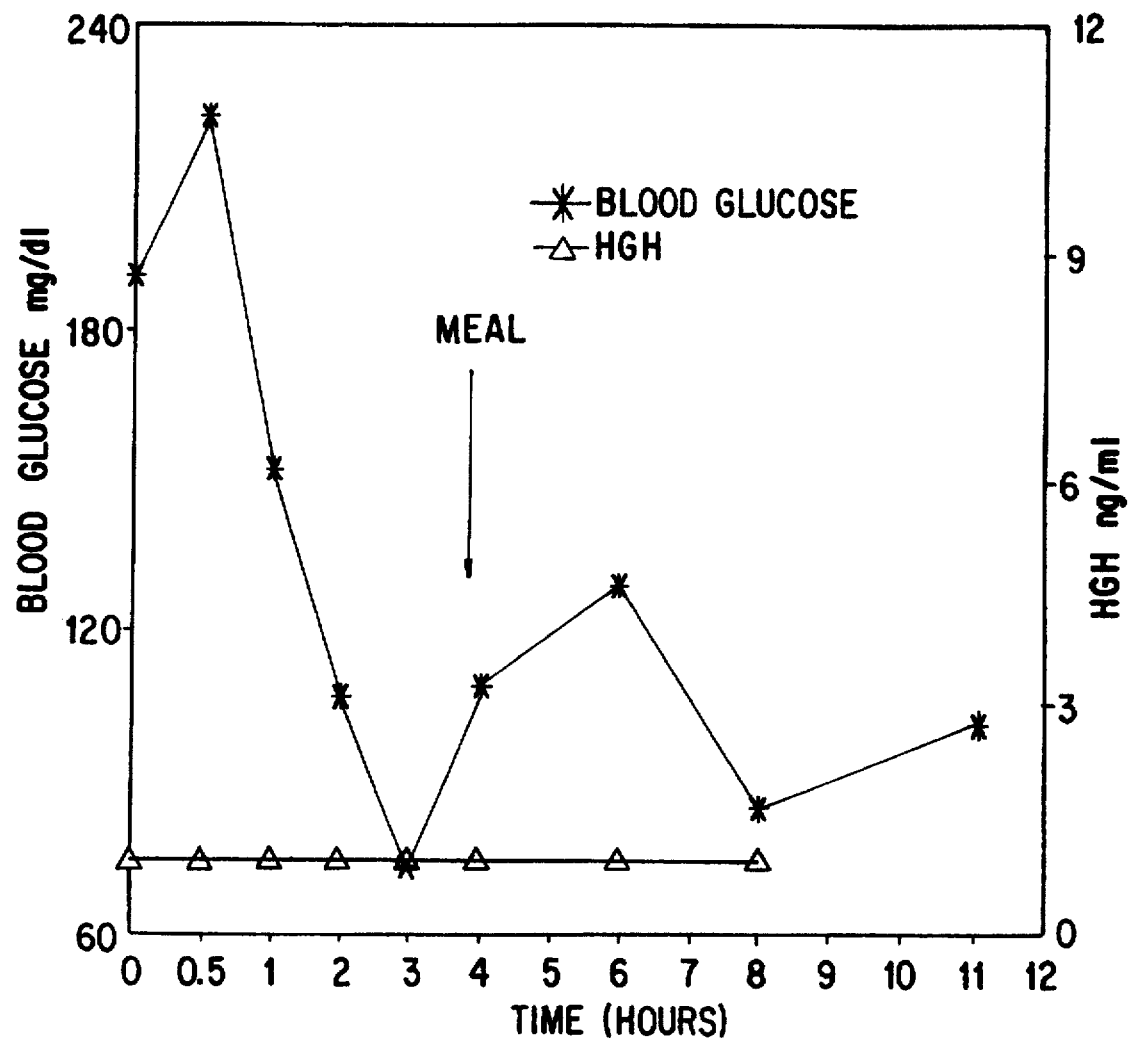
FIG. 9 shows for individual subject YKS the bioavailability over time of the control; orally administered recombinant human growth hormone.

According to a first aspect of the invention, there is provided a pharmaceutical composition comprising a proteinaceous or other biologically active compound and a lecithin or a lecithin precursor.

The proteinaceous compound may be replaced by (or supplemented with) any other biologically active compound. The mode of action in such cases is believed to be analogous to that set out above. The biologically active compound and the lecithin precursor will generally be in some form of association with each other.

Lecithin can integrate into chylomicra, particularly into their membranes. The use of other compounds, or precursors of them, which can similarly so integrate is also within the scope of the invention. The discussion in this specification relating to lecithin or its precursors may be taken to apply to this more general class of compounds *mutatis mutandis*.

The lecithin precursor may form lecithin within the intestinal epithelium of man or other animals, and so the proteinaceous compound will be in association with the lecithin as formed as a lecithin-protein complex (such as lecithin-insulin). Lecithin formed in this way within the intestinal epithelium may form the surface membrane of chylomicra as well as covering up to 80% of the surfaces of apolipoproteins, such as apoprotein-A, -B, -C and -E. Thus, optionally using appropriate absorbtion enhancers for the phospholipo-protein complex, the complex may be absorbed into the intestinal epithelium; lecithin is then synthesised (and the complex then becomes a lecithin-protein complex); and the lecithin may then cover chylomicron cores as well as those apoproteins attached to chylomicra. The lecithin may then be released into lymphatic vessels, drained into the thoracic duct (and those lecithin-protein complexes still attached to chylomicra may form part of the remnant chylomicra), channelled into the liver and from there released into the circulating blood. The lecithin is believed effectively to carry the protein with it into general circulation by this means.

Lecithin may be formed in vivo by a variety of different routes. Some of these are as follows. First, the α-glycerol pathway may be used; sn-Glycerol-3-phosphate is used as a precursor in this pathway, as are phosphatidates and diglycerides. Secondly, lecithin may be synthesised by the action of cholinephosphotransferase; choline, phosphocholine, cytidine diphosphocholine and diglycerides are used as precursors in this route. Thirdly, lecithin may be synthesised from other phosphatides such as phosphotidyl ethanolamine. Fourthly, lecithin may be synthesised from triglyceride and indeed lecithin breakdown products or by transesterification processes.

The term "biologically active material" includes, in particular, pharmaceutically active proteinaceous materials. The proteinaceous material may be a pure protein, or it may comprise protein, in the way that a glycoprotein comprises both protein and sugar residues. The material may be useful in human or veterinary medicine, either by way of treatment or prophylaxis of diseases or their symptoms, or may be useful cosmetically or diagnostically. Examples of proteinaceous biological material which can be provided as orally or rectally administrable formulations in accordance with this invention include protein hormones such as insulin, calcitonin and growth hormone, whether from human or animals or semi- or totally synthetically prepared, erythropoietin or haematopoietin, plasminogen activators and their precursors, such as t-PA, urokinase, pro- urokinase and streptokinase, interferons including human interferon alpha, interferon beta and interferon gamma, interleukins including IL-1, IL-2, IL-3, IL-4 and IL-5 colony stimulating factors including G-CSF and GM-CSF and blood factors including Factor VIII.

It is to be emphasised, however, that the invention is not limited to the formulation of proteinaceous compounds: many non-proteinaceous pharmaceutical agents may successfully be formulated by means of the present invention. For example, non-steroidal anti-inflammatory drugs (NSAIDs) such as indomethacin and other agents including gentamycin may appropriately be formulated.

However, in view of the co-formulation of the biologically active material with, for example, phospholipids in this invention, it is desirable that the active material is not one that irreversibly forms a covalent bond with a phospholipid, or indeed any of the other components of the formulation, as this may in some circumstances impair biological activity and/or availability. Having said that, it is not believed that there is any problem on this account with the formulation by means of the invention of any of the active molecules specified above. The association between the active compound and the lecithin or precursor may be in the nature of a non-covalent complex. Such a complex may involve hydrogen bonding, van de Waals interations, ionic interactions and/or lipid-lipid interactions.

While it is not believed that there is any particular molecular size constraint on biologically active materials that can be formulated by means of the present invention, it will be apparent from the exemplary but non-limiting selection of biologically active materials given above that the invention is particularly suitable for formulating macromolecules. The molecular weight of such macromolecules may be about 1 kDa or above 5 kDa, about 10 kDa or above, or even about 15 kDa or above. Again, while it is not believed that hydrophilicity or hydrophobicity (lipophilicity) of the biologically active material is particularly critical, the invention readily enables the formulation of hydrophilic molecules such as insulin, calcitonin (especially salmon calcitonin) and growth hormones or somatotropin (especially porcine somatotropin), all of which (particularly salmon calcitonin) are so hydrophilic as to be hygroscopic.

The amount of biologically active material present in a formulation of the invention will naturally depend on the nature of the material and will be such an amount as to make prescription of conveniently administrable amounts a practicable proposition. Bearing these considerations in mind, formulations in accordance with the invention may contain from 1 µg, 10 µg, 0.1 mg or 1 mg per liter to 1, 10 g or 100 g per liter.

The present invention involves derivatives or constituent parts or groups of phospholipids or other compounds which are capable of acting as precursors for the in vivo synthesis of lecithin at the human or other animal intestinal epithelium; the lecithin in turn forms at least part of the membrane to the chylomicron core. It is believed that under the conditions of administration, the membrane-integrating compounds cause the associated biologically active material to be integrated into a lecithin membrane covering for example a chylomicron core; the membrane is composed primarily of phospholipid, as discussed above. Because chylomicron membranes are phospholipid-rich, phospholipids are very suitable materials with which to formulate biologically active materials in accordance with the invention.

The lecithin precursors should not be such as to cause deterioration of the biologically active material; for example, it has been reported that some fatty acids, such as oleate and stearate, may interact adversely with porcine somatotropin, so a certain but routine amount of care should be used when selecting the phospholipids, phospholipid derivatives or other membrane-integrators or precursors to be used. The selection will however be well within the capabilities of those skilled in the art.

Phospholipids are the lecithin precursors of choice. Phospholipids are glyceryl triesters in which one of the ester functions is an optionally substituted phosphoric acid. Phospholipids preferred for use in the present invention have the following general formula:

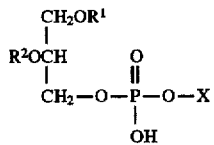

wherein each of $R^1$ and $R^2$ independently represents an acyl group of for example 10, 12 or 14 to 26 carbon atoms which is optionally mono- or poly-unsaturated and X represents a hydrogen atom or a phospholipid head group.

The phospholipid head group may be any group that is capable of forming a physiologically acceptable phospholipid. Examples of phospholipids include:

diacyl phosphatidyl glycerols, such as:
 dimyristoyl phosphatidyl glycerol (DPMG),
 dipalmitoyl phosphatidyl glycerol (DPPG), and
 distearoyl phosphatidyl glycerol (DSPG);
diacyl phosphatidyl cholines, such as:
 dimyristoyl phosphatidylcholine (DPMC),
 dipalmitoyl phosphatidylcholine (DPPC), and
 distearoyl phosphatidylcholine (DSPC);
diacyl phosphatidic acids, such as:
 dimyristoyl phosphatidic acid (DPMA),
 dipalmitoyl phosphatidic acid (DPPA), and
 distearoyl phosphatidic acid (DSPA); and
diacyl phosphatidyl ethanolamines such as:
 dimyristoyl phosphatidyl ethanolamine (DPME),
 dipalmitoyl phosphatidyl ethanolamine (DPPE), and
 distearoyl phosphatidyl ethanolmine (DSPE).

Other examples include, but are not limited to, derivatives of ethanolamine (such as phosphatidyl ethanolamine, as mentioned above, or cephalin), serine (such as phosphatidyl serine) and 3'-O-lysyl glycerol (such as 3'-O-lysyl-phosphatidylglycerol).

More than one phosphatidyl group may be attached to a single phospholipid head group; for example, two phosphatidyl moieties may be attached to a single glycerol residue as in diphosphatidyl glycerol or cardiolipin. When X represents a hydrogen atom, the phospholipid is a phosphatidic acid such as L-α-phosphatidic acid bimyristoyl.

Phospholipids useful in the present invention include synthetic and natural phospholipids, whether as single components or as a mixture of two or more components. Preparations of ostensibly pure natural phospholipids will rarely if ever actually conain a single species of phospholipid, but this factor is not believed to be critical for the purposes of the present invention.

Particularly preferred phospholipids include 1,2-dimyristoyl-sn-glycerol-3-phosphocholine, which may be in the form of the monohydrate and L-α-phosphatidic acid bimyristoyl, which may be in the form of the sodium salt.

Other precursors of lecithin may be used instead or in addition.

In compositions of this invention, the biologically active material may be in association with the lecithin precursor. While the precise nature of this association is not necessarily critical, it is believed that it may involve non-covalent interactions, particularly hydrogen bonding and hydrophobic interaction, much in the same way that lipoproteins conventionally present in chylomicron or other phospholipid membranes are bound.

In the presence of one or more high hydrophile/lipophile balance (HLB) surfactants, such as those having an HLB value above 10 or even above 14, the biologically active material, in association with the lecithin precursor, may form a hydrophilic complex which passes readily in to the enterocytes (gut epithelial wall cells). Within the enterocytes, a lecithin precursor is recognised as such, for use in lecithin synthesis. In this way, the precursor and the associated biologically active material appears to avoid the lysosome and is converted into a complex of biologically active material and membrane integrating compound (such as lecithin). Such a complex may replace or supplement the lecithin which forms the outer-layer membrane covering about 80% or more of the surface of the chylomicron core.

In the circulating blood, surface proteins and phospholipids may exchange with other lipo-proteins. So at least a portion of a protein administered by means of the present invention may circulate in the blood as a phospholipoprotein separated from a chylomicron with which it was originally or previously associated. Some of the phospholipoprotein may be released into the circulating blood in free form and, in part, may be passed to the liver attached to chylomicron remnants. The speed and extent of the phospholipid/protein exchange may be influenced by various factors, including altering the phospholipid chain length.

Formulations in accordance with the invention may generally also contain a hydrophilic liquid, which will usually be aqueous and may be water; physiological or phosphate-buffered saline may satisfactorily be used. A water miscible solvent may be present, for example to aid in formulating. Ethanol or another suitable simple organic solvent may therefore be present. The nature of the solvent used will depend on the active material. The hydrophilic liquid may be as water:solvent mix, for example in v/v proportions of 0.5:1 to 2:1, although the presence of a non-aqueous solvent is not necessarily preferred.

Broad and preferred percentage compositions (which will generally be weight/weight percentages, but may be weight/volume or even volume/volume percentages) of components are given below, providing always that the total does not exceed 100%:

|  | Broad | Preferred |
| --- | --- | --- |
| Precursor/active | 0.1–25 | 1–10 |
| Hydrophilic liquid | 10–99 | 50–95 |

|  | More Preferred | Optimal |
| --- | --- | --- |
| Precursor/active | 2.5–8 | 4 |
| Hydrophilic liquid | 65–90 | 89 |

Formulations in accordance with the invention may contain a hydrophilic surfactant (for example with an HLB greater than 10). This may have the effect of promoting the formation of a complex between the biologically active compound and the lecithin precursor (particularly for synthesised lecithin or lecithin precursors in the gut epithelium in humans and certain other animals such as pigs), and/or of conferring a broadly hydrophilic character on such a complex. The hydrophilic surfactant may be present in an amount up to 10% (w/v or v/v), preferably from 1 to 5%, typically from 1.5 to 4%, for example about 2.4% or 2.5%.

One further component that is often highly desirable is a protease inhibitor, which may be in the form of one or more individual protease inhibitors. Protease inhibitors useful for the present invention can broadly be divided into two categories. First, there is the category of protease inhibitors which are useful in limiting or preventing the degradation of the biologically active material if it is proteinaceous. Such protease inhibitors should have the effect of inhibiting proteolytic enzymes found in the gastrointestinal tract, such as trypsin, chymotrypsin and carboxypeptidase. In the case of insulin, the protease inhibitors will generally be inhibitory of the class of enzymes that have come to be known as insulinase, which includes the enzyme trans-sulphatase. Suitable sources of trypsin inhibitors can be extracted from soy beans or egg white (ovomucoid). Secondly, if apoprotein is present in formulations in accordance with the invention, it is desirable to add protease inhibitors to reduce the amount of degradation of the apoprotein before it reaches the intestinal mucosa. Generally speaking, similar protease inhibitors can be used as for the protection of proteinaceous biologically active materials, and so a single protease inhibitor may serve both functions. Protease inhibitors may be added to the association or complex between the biologically active material and the membrane integrator or precursor (for example the phospholipids); for convenience they may be added to the hydrophilic phase, where two phases are present. The choice of the amount of protease inhibitor to be added will be well within the skill of a person skilled in the art, but generally will be in amounts up to about 0.1% w/v, or even 0.5% w/v. Aprotinin may be added in an amount up to 10 million IU, preferably 0.5 to 5 million IU, typically 1.5 to 4 million IU, for example 3.0 million IU, but the exact amount used may depend on the actual activity of the biologically active material.

It will in many cases be advantageous to administer the complex of biologically active material and membrane inegrator or precursor (the phospholipoprotein complex in the preferred embodiment), together with the optional but preferred hydrophilic surfactant and protease inhibitor, suspended in, or made into an emulsion or microemulsion containing lipophilic material including a low HLB surfactant (for example having an HLB value of less than 4). The lipophilic material may (but does not necessarily) include those material known to form chylomicra in vivo; such material includes but is not limited to cholesterol, cholesterol ester(s), lecithin and/or other phospholipids or saturated or mono- or polyunsaturated fatty acids (for example having a carbon content of $C_{16}$ to $C_{24}$), which may optionally be esterified as a glycerol ester to form a mono-, di- or triglyceride. Alternatively, the essentially hydrophilic phospholipo- protein (or other complex) may simply be mixed with suitable oils, particularly vegetable oils, such as medium chain triglyceride (MCT) oil or any other appropriate oil, plus one or more suitable surfactants having a low HLB value (for example less than 4). Suitable surfactants include lysolecithin derivatives and other essentially lipophilic materials.

The hydrophilic phospholipoprotein (or other complex) may be appropriately enteric coated and may be orally administered. However, experiments suggest that it is preferable to mix the complex with a suitable oil or precursors so as to channel the active material into the villae of the small intestine tract from where it is absorbed through the villae and drained into the lymphatic system.

Broad and preferred percentage compositions (which will generally be weight/weight percentages, but may be weight/volume or even volume/volume percentages) of the lipophilic material for general purposes are given below, providing always that the total does not exceed 100%:

|  | Broad | Preferred |
| --- | --- | --- |
| Cholesterol | 0.1–40 | 1–10 |
| Lecithin (or other phospholipid) | 0.1–60 | 1–15 |
| Lipophilic surfactant | 0.1–40 | 3–10 |
| Non-esterified fatty acid | 0–95 | 20–90 |
| Cholesterol ester | 0–10 | 0–5 |

|  | More preferred | Optimal |
| --- | --- | --- |
| Cholesterol | 2–8 | 6 |
| Lecithin (or other phospholipid) | 4–10 | 8 |
| Lipophilic surfactant | 4–8 | 6 |
| Non-esterified fatty acid | 35–75 | 50 |

Some lipophilic-phase miscible organic solvent may be present, possibly as an aid in formulation. The nature of the solvent will depend on the other materials present. Ethanol is often suitable. The amount of solvent may be, for example from 5 to 50% v/v, based on the volume of the lipohpilic phase.

When the phospholipoprotein or other complex is formulated as an emulsion or microemulsion with a lipophilic phase as discussed above (usually as a water-in-oil system) it is not essential for any other ingredients to be present although, as a matter of practice, it is usually highly convenient for other ingredients to be added. An optional ingredient is a stabiliser for the biologically active material. The precise nature of the stabiliser, if present, will of course depend on the nature of the biologically active material itself. For example, there are a number of well defined stabilisers for insulin, which can be advantageously be incorporated in insulin-containing formulations in accordance with the invention. Examples include hydroxypropyl cellulose (HPC), calcium salts and citric acid and its salts. Calcium is known not only to stabilise insulin but also to have an additional beneficial effect of increasing the porosity of cell membranes, thereby facilitating entry of the active material into the intestinal wall cells. As the biologically active material is added in the hydrophilic phase, the stabiliser will for preference normally be added in that phase too. The amount of stabiliser to be present will again depend on its nature and the nature of the biologically active material; the choice of the amount will be well within the capabilities of a person skilled in the art but will often be in amounts up to about 1 or 2% w/v.

It may be desirable in some instances to incorporate emulsification aids, which may be conventional emulsification aids used in the preparation of emulsions. Some emulsification aids are surfactants, and surfactants useful for this purpose are not restricted to any particular HLB values. Useful emulsification aids include cholesterol, stearic acid, sodium stearate, palmitic acid, sodium palmitate, oleic acid, sodium oleate, glyceryl monooleate, polyoxyethylene 50 stearate, polyoxyethylene 40 stearate, polysorbate 20, polysorbate 40, polysorbate 60, polysorbate 80, propylene glycol diacetate, and propylene glycol monostearate.

Emulsification aids may be present in either or both of the lipophilic and hydrophilic phases. The amount of emulsification aid to be present, if desired, will simply be enough to assist in adequately obtaining a stable formulation. The exact amount can be determined by a person skilled in the art; generally speaking they can be used in amounts of from 0 to 15% w/v, for example 0.1 to 5% w/v of the formulation as a whole. It may be appropriate to provide, say from 1 to 5% in the hydrophilic phase of the same or a different surfactant. It has been found to be particularly appropriate to add polysorbate 80 to the lipophilic phase and polyoxyethylene 40 stearate to the hydrophilic phase.

Formulations in accordance with the invention can contain various preservatives. Two particularly useful categories of preservatives are antioxidants and antimicrobial agents. Antioxidants are particularly useful because certain compounds suitable for use in formulations of the invention are prone to degradation by autoxidation. Although this problem can be avoided by preparing formulations in accordance with the present invention under an inert atmosphere, such as nitrogen, this is a somewhat inconvenient and expensive process and so it is often preferred to add chemical anti-oxidants. Suitable pharmaceutically acceptable anti-oxidants include propyl gallate, butylated hydroxyanisole, butylated hydroxytoluene, ascorbic acid or sodium ascorbate, DL- or D-α-tocopherol and DL- or D-α-tocopheryl acetate. The anti-oxidant, if present, may be added to formulations in accordance with the invention in an amount of up to, for example, 0.1% (w/v), preferably from 0.0001 to 0.3%. The appropriate phase for the antioxidant will naturally depend on the nature of the antioxidant. Generally lipophilic antioxidants such as α-tocopherol may appropriately be incorporated into the hydrophobic phase, whereas hydrophilic antioxidants such as ascorbic acid may be incorporated into the hydrophilic phase.

Sesame oil, preferably as a refined chemical oil, may be added to formulations of the invention, as it has anti-oxidant activity. Sesame oil has the further advantage that it improves the flavour of the formulations, thereby improving patient compliance. Sesame oil may be present in an amount of from 0.1 to 3% w/v preferably 5 to 20% w/v of the final liquid formulation; it will usually be added to the lipophilic phase.

Antimicrobial preservatives which may be used, generally in amounts of up to about 3% w/v, preferably from about 0.5 to 2.5%, of the total formulation, include methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, cresol, p-chloro-m-cresol, chlorobutanol, phenylmercuric acetate, phenylmercuric borate, phenylmercuric nitrate and benzylalkonium chloride. Antimicrobial agents can be added to either phase as required or appropriate.

Although not essential, it may be practical or convenient to improve trans-lymphatic absorbtion of the phospholipoprotein or other complexes in humans and certain other species when formulations of the invention are in two-phase form. Two-phase systems in accordance with the invention include water-in-oil (ie hydrophilic-in-lipophilic), water-in-oil-in-water, oil-in-water and oil-in-water-in-oil systems.

Two-phase systems can in general be prepared by intimate admixture of the hydrophilic and lipophilic phases. Two-phase systems in accordance with the invention may be emulsions or microemulsions. The volume:volume ratio of the hydrophilic phase:lipophilic phase will generally be in the range of from 0.2:1 to 5:1, typically from 0.5:1 to 2:1.

To form emulsions or microemulsions, it is sometimes necessary to use two different surfactants, one being hydrophilic and having a high hydrophile-lipophile balance (HLB), and the other being more lipophilic (as described above), and having a low HLB. Hydrophilic surfactants useful in the present invention, when present, have a high HLB of at least 10 or a very high HLB of at least 17 and possibly approaching 20. Lipophilic surfactants used in the invention have a low HLB of, for example, less than 10. Preferably, the lipophilic surfactant has an HLB value of less than 7 or even less than 4.

As general guidance it is preferred that each of the surfactants used in the preparation of formulations of this invention be selected from those surfactants classified as anionic or nonionic. These surfactants are particularly useful in pharmaceutical systems for their compatibility, stability, and non-toxicity. Surfactants generally suitable for the various purposes in the present invention include:

long chain ($C_{16}$ to $C_{24}$) fatty acids, e.g. palmitic acid, stearic acid and oleic acid;

esters of long chain ($C_{16}$ to $C_{24}$) fatty acids, e.g. sodium palmitate, sodium stearate and sodium oleate;

sodium lauryl sulphate;

fatty acid esters of polyethylene glycol, e.g. polyethylene glycol mono- or di-stearate;

propylene glycol and fatty acid esters of propylene glycol, e.g. propylene glycol monostearate;

glycerine and fatty acid mono- or poly-glycerides, such as glyceryl monostearate;

polyoxyethylene fatty acid esters, ethers and amines, e.g. polyoxyethylene mono- and di-stearate, and polyoxyethylene lauryl ether;

polyoxyethylene sorbitan esters, e.g. polyoxyethylene sorbitan monolaurate, monopalmitate, monostearate or mono-oleate;

polyoxyethylene alkyl phenols and alkyl phenyl ethers;

polyoxyethylene castor oil;

sorbitan fatty acid esters;

the polysorbates; stearylamine; triethanolamine oleate;

vegetable oils, e.g. sesame seed oil or corn oil;

cholesterol; and
tragacanth.

The surfactants of choice will of course be those which are currently on the approved list for pharmaceutical use and will have appropriately low LD$_{50}$ values. There follows a list of certain exemplary surfactants, together with their HLB values and, where known, their LD$_{50}$ values.

Examples of suitable high HLB surfactants are as follows:

| Chemical Identity | | HLB | LD$_{50}$ g/kg |
|---|---|---|---|
| Polyethylene Glycol Esters | | | |
| PEG-monostearate | | 19.1 | ? |
| Polyoxyethylated Glycol Monoethers | | | |
| POE(23) | lauryl ether | 17.0 | 9 |
| Polyoxyethylated Fatty Acids | | | |
| POE(40) | lauric aicd | 17.9 | ? |
| POE(100) | lauric acid | 19.1 | ? |
| POE(40) | oleic acid | 17.4 | ? |
| POE(100) | oleic acid | 18.8 | ? |
| POE(40) | stearic acid | 17.8 | ? |
| POE(50) | stearic acid | 17.9 | >25 |
| POE(100) | stearic acid | 18.8 | 25 |

Examples of suitable low HLB surfactants are as follows:

| Chemical Identity | | HLB | LD$_{50}$ g/kg |
|---|---|---|---|
| Glycerol Esters | | | |
| Glycerol monooleate | | 3.8 | ? |
| Polyoxyethylated Glycol Monoethers | | | |
| POE(4) | lauryl ether | 9.5 | 9 |
| POE(2) | cetyl ether | 5.3 | 22 |
| POE(2) | stearyl ether | 4.9 | >25 |
| POE(2) | oleyl ether | 4.9 | 25 |
| Polyoxyethylated Fatty Acids | | | |
| POE(4) | lauric acid | 9.3 | ? |
| POE(4) | oleic acid | 7.7 | ? |
| POE(4) | stearic acid | 7.7 | ? |
| Sorbitan Fatty Acid Esters | | | |
| Sorbitan monolaurate | | 8.6 | 41 |
| Sorbitan monopalmitate | | 6.7 | >16 |
| Sorbitan monostearate | | 4.7 | 31 |
| Sorbitan tristearate | | 2.1 | >16 |
| Sorbitan monooleate | | 4.3 | >40 |
| Sorbitan sesquioleate | | 3.7 | ? |
| Sorbitan trioleate | | 1.8 | >40 |
| Sorbitan monoisostearate | | 4.7 | ? |
| Polyoxyethylated Sorbitan Fatty Esters | | | |
| POE(4) | sorbitan monostearate | 9.6 | >40 |
| POE(5) | sorbitan monooleate | 10.0 | >37 |
| Polyoxyethylated Castor Oils | | | |
| POE(10) | castor oil | 6.3 | ? |
| POE(10 | hydrogenated castor oil | 6.3 | ? |
| Poloxamers | | | |
| POE(7) - POP (17) | (L42) | 8 | ? |
| POE(4) - POP (23) | (L61) | 3 | ? |
| POE(10) - POP (23) | (L62) | 7 | ? |
| POE(27) - POP (23) | (L64) | 7 | ? |
| POE(6) - POP (30) | (L81) | 2 | ? |
| POE(19) - POP (37) | (L92) | 5.5 | ? |
| POE(8) - POP (43) | (L101) | 1 | ? |
| POE(32) - POP (43) | (P103) | 9 | ? |
| POE(10) - POP (53) | (L121) | 0.5 | ? |

It should be noted that mixtures of surfactants can often be used in place of single surfactants in the present invention. For example, instead of a single hydrophilic surfactant, a mixture of two or more relatively hydrophilic surfactants could be used; the effective HLB of the mixture should, however, be greater than 10. By "effective HLB" is meant that the hydrophile-lipophile balance of the mixture of surfactants should be equivalent to a single surfactant having an HLB of greater than 10. Similarly, mixtures of lipophilic surfactants can be used in place of a single lipophilic surfactant. Again, the effective HLB of the lipophilic surfactants should be less than 10.

The choice of the amount of surfactant to be used in formulations of the present invention is left as a matter of choice to those skilled in the art. Naturally, precise amounts that will be optimal in each case will depend very much on the precise nature of the surfactants used and what other ingredients in the formulations are present. Nevertheless, as general guidance, the amount of hydrophilic surfactant, when present, will generally be in the range (based on the total volume of the formulation) of from 0.1 g to 50 g per liter, with a range of from 0.5 to 25 g per liter usually being preferred and from 1 g to 10 g per liter often being optimal. The lipophilic surfactant has been discussed above in relation to the oil phase of the microemulsion. It will generally be present in an amount of from 0.1 g to 100 g per liter, with a range of from 0.5 g to 50 g per liter being preferred and a range of from 2 g to 25 g per liter often being optimal, with the figures again being based on the total volume of the formulation.

Compositions in accordance with the invention may be prepared, most broadly, by admixture of the ingredients. According to a second aspect of the invention, there is therfore provided a process for the preparation of a composition as described above, the process comprising admixing the ingredients of the composition.

It is generally preferred for the active (usually proteinaceous) compound and the lecithin precursor to be admixed first. This enables the "phospholipo-protein" complex to be formed in preferred embodiments.

As discussed above, some compositions in accordance with the invention involve two phases. A preferred process for preparing such compositions comprises:

(i) providing a hydrophilic phase comprising a biologically active substance and a lecithin precursor; and (ii) forming a two-phase system including the hydrophilic phase, optionally in conjunction with one or more absorbtion enhancers.

Because of the inherent thermodynamic stability of certain emulsions and microemulsions, liquid formulations in accordance with the invention can simply be prepared by mixing the hydrophilic and lipophilic phases, which in turn can be prepared by mixing their respective ingredients together. Kinetic considerations, however, suggest that as a practical matter certain steps be taken to ensure the rapid and effective formation of emulsion or microemulsion formulations in accordance with the invention. In particular, during or after the hydrophilic and lipophilic phases have been added together, a microemulsion can be speedily formed by the use of a microfluidiser, and an emulsion can be prepared by using an appropriate apparatus which gives intimate admixture.

It will be appreciated that some formulations in accordance with the invention, particularly two-phase formulations, are likely to be liquid. However, they can be converted into solid, powdery forms by conventional methods. In general, the liquid form may be coated onto solid carrier powders by using a fluidiser bed or similar equipment (such as a SPIR-A-FLOW apparatus). (The expression SPIR-A-FLOW is a trade mark.) Powder or granules resulting from this operation may be packed into hard gelatin capsules, which may then be enteric coated if desired. Alternatively, the resulting powder or granules may be made into granules sized about 1 to 2 mm, which can then be enteric coated and placed into hard gelatin capsules. Alternatively, the liquid formulation may be packaged into soft gelatin capsules, which, if required and feasible, can be enteric coated. Suitable enteric coating materials are known, for example, from "Remington's Pharmaceutical Sciences", 15th Edition, pp. 1614–1615 (1975); 2nd Edition, pp 116–117, 371–374 (1976); and "Hagers Handbuch der Pharmazeutischen Praxie", 4th Edition, Volume 7a (Springer Verlag 1971), pages 739 to 742 and 776 to 778.

Formulations in accordance with the invention can therefore be administered orally, but in a wide variety of different ways, for example as a liquid, as a soft gelatin capsule, as a hard gelatin capsule, as a pressed tablet (which may also be enteric coated) and in other ways. Furthermore, high plasma levels as well as high levels at the supposed target receptors indicate that biologically active materials administered by means of the invention have high bioavailability and that the active material is bioactive.

For rectal administration, liquid or solid formulations can be administered as an enema or in suppository form. The suppository base may be cocoa butter or any other suitable material.

According to a further aspect of the invention, there is therefore provided a method of treating a human or other animal, comprising the oral or rectal administration of a formulation in accordance with the first aspect of the invention. In particular, the invention extends to the treatment of diabetes by the rectal or preferably oral administration of a formulation in accordance with the invention in which the biologically active material is insulin.

The invention also extends to the use of the ingredients of formulations in accordance with the first aspect of the invention in the preparation of an orally or rectally administrable formulation for the treatment or prophylaxis of disorders treatable or controllable by a biologically active material.

In particular, insulin can be used in the preparation of a formulation for the treatment or control of diabetes. Salmon calcitonin can be used in the treatment of high bone turnover (for example in Paget's disease of the bone), acute hypercalcaemia associated with malignancy and osteoporosis. Erythropoietin can be used in the treatment of anaemia arising from chronic usage of either extracorporeal renal dialysis devices or anti-cancer chemotherapeutics or other causes. Porcine somatotropin can be administered to pigs to reduce the raising time of pigs and possibly to reduce the thickness of back fat. Human growth hormone can be used to treat children with a retarded growth rate.

The invention will now be illustrated by a number of non-limiting examples.

EXAMPLE 1

In this example, insulin is the biologically active ingredient and a formulation containing a phospholipo-insulin complex is prepared.

At room temperature, bovine insulin (2 to 20 mg of bovine insulin crystalline or powder having about 22 to 26 IU activity per mg) is added 1.0 to 3.0 g of soybean lecithin, egg yolk lecithin, L-α-phosphatidic acid bimyristoyl (sodium salt), and/or 1,2-dimyristoyl-sn- glycerol-3- phosphocholine monohydrate and dissolved in either 0.9% benzyl alcohol or 0.9% sodium chloride (150 ml) in presence of 400 mg of aprotinin (@ 3,000,000 Kallikrein inactivator units), adjusted to pH @ 2.3 with citric acid solution in room temperature. A non-ionic surfactant, preferably polyoxy-40-stearate (4 g) is added to the above 'phospholipid-insulin' compound.

Under gentle and constant stirring at room temperature, the above phospholipo-insulin solution is slowly added into an oil-phase solution comprising pre-chylomicron complexes (which are complexes of phosphatidylcholine; mono-, di-, and/or tri-glyceride; cholesterol and others), a non-ionic surfactant with an HLB value less than 4.0 and one or more anti-oxidants.

The above "water-in-oil" emulsion is passed through a microfluidizer at 5° to 10° C., at 100,000 PSI or more for two consecutive times. Thus a "water-in-oil" microemulsion form of the phospholipo-insulin complex was prepared. Each 400 ml of this microemulsion contains the following ingredients:

| Chemical Composition | per 400 ml Microemulsion |
| --- | --- |
| Bovine Insulin | 87,000 IU |
| Dimyristoyl-glycerol-phosphocholine* | 1.0 g |
| Aprotinin | 2,000,000 KIU |
| Polyoxy-40-stearate | 2.9 g |
| Cholesterol | 11.6 g |
| Glycerolmonooleate | 10.6 g |
| Oleate | 92.5 g |
| Polysorbate 80 | 6.8 g |
| d-alpha-tochopherol | 1.2 g |
| Citric acid | 0.9 g |
| Physiological saline solution | To 400 ml |

EXAMPLE 2

In this example, the biologically active compound is erythropoietin (EPO) and a phospholipo-erythropoietin complex is prepared as in Example 1 above. Also, one-half of EPO was directly added into the water-phase of the two-phase (microemulsion) system. Thus, in this example, the proteinaceous compound was not only bound with phospholipids, but also added directly into the water-phase of microemulsion system.

Erythropoietin (EPO) was supplied by the Chugai Pharmaceutical Company, Ltd. of Tokyo, Japan (Lot No. R9H05). One aliquot had a protein concentration of 0.936 as measured by amino acid analysis, and 1.018 mg as measured by RP-HPLC analysis, and had an in vivo specific activity of 180,000 IU in pH7.2 phosphate buffer solution). At room temperature, the EPO aliquot is divided into two halves. To the first half of the EPO aliquot, from 0.004 to 0.007 mg 1,2-dimyristoyl-sn-glycerol-phosphocholine monohydrate per 1000 IU EPO was added and the resulting mixture dissolved in 50 ml of 0.9% physiological saline solution; the pH was adjusted to 7.3 with 0.1M phosphate buffer (pH7.8) in presence of 3000 to 4000 IU of aprotinin (per 1000–15000 IU EPO). The remaining half of EPO was dissolved in 100 ml of physiological saline solution, adjusted pH to 7.3 as above, and then aprotinin (as above) and a non-ionic surfactant having an HLB value above 7.0, such as polyoxy-40-stearate, were added at concentrations of 0.0044 to 0.00044 mg per 1000 IU EPO; emulsion-stabilisers and viscosity increasers, such as hydroxypropyl cellulose-SL, may be dissolved into the above solution at room temperature.

Under gentle and constant stirring at room temperature, the phospholipo-EPO complex and the EPO-containing 'water-phase solution' is slowly added into an oil-phase solution containing cholesterol, lecithin, glycerol monooleate (a non-ionic surfactant having HLB value of less than 4.0) and anti-oxidants.

The above water-in-oil emulsion was passed through a microfluidizer-emulsifier once in the cold. For each 1000 IU of EPO, the resulting W/O EPO microemulsion may contain the following:

| Chemicals | mg/1000 IU EPO |
| --- | --- |
| EPO (Lot No. R9H05) | 1000 IU |
| 1,2,-Dimyristoyl-sn-glycerol-phosphocholine monohydrate | 0.0056 |
| Hydroxypropylcellulose-SL | 0.880 |
| Polyoxy-40-Stearate | 0.440 |
| Aprotinin | 3000 KIU |
| Cholesterol | 1.880 |
| Lecithin, Egg Yolk | 3.800 |
| Glycerolmonooleate | 1.680 |
| d-alpha-Tocopherol | 1.180 |
| oleic acid | 15.000 |
| Tween-80 | 1.06 |
| Ethanol | 7.00* |

(*To be evaporated in most part).

EXAMPLE 3

In this example, a phospholipo-porcine somatotropin (pST) complex and formulation was prepared according to the present invention.

Porcine somatotropin (pST) crystalline powder (pST Lot No. 7368C-25Q) was supplied by American Cyanamid Company, Agricultural Research Division, of Princeton, N.J., USA. At room temperature, pST is added to a 0.9% saline solution containing phospholipids, such as 1,2-dimyristoyl-sn-glycerol-3-phosphocholine mono- hydrate, L-alpha-phosphatidic acid bimyristoyl (sodium salt), egg yolk lecithin, and/or soybean lecithin. A non-ionic surfactant having an HLB value of above 7.0 is also added in presence of aprotinin, a trypsin-inhibitor, in physiological saline solution.

The pH of water-phase solution is adjusted, if necessary, to pH 7.2 with 0.1M NaCl/10 mM sodium phosphate buffer. Under gentle and constant stirring at room temperature, the above phospholipo-pST solution is slowly added into an oil-phase solution containing a lecithin-cholesterol-glycerol-monooleate mixture; the resulting mix is run through a microfluidizer-emulsifier twice in cold. Each ml of pST microemulsion contains the following:

| Chemicals | mg/ml pST Emulsion |
| --- | --- |
| Lecithin | 12.5 |
| Cholesterol | 30.48 |
| Soy Lecithin | 187.43 |
| 1,2-dimyristoyl-sn-glycerol-3-phosphocholine monohydrate | 1.91 |
| L-alpha-phosphatidic acid bimyristoyl sodium salt | 0.095 |
| Oleic acid | 242.29 |
| d-alpha-tochopherol | 7.62 |
| Glycerol-1-monooleate | 27.81 |
| Hydroxypropylcellulose-L | 14.48 |
| Polyoxy-40-stearate | 7.62 |
| Aprotinin | 2850 KIU |

| Chemicals | mg/ml pST Emulsion |
| --- | --- |
| Tween-80 | 17.91 |
| pH adjusted to 7.2 with sodium phosphate buffer (10 mM) | |

EXAMPLE 4

Recombinant human growth hormone (r-hGH; Batch No. 9-08 P-508-2, 16th Aug. 1989) was supplied by SmithKlein Beecham of Philadelphia. The r-hGH was incorporated into a pharmaceutical formulation broadly as in the other examples. Specifically, r-hGH (500 mg powder) was bound and dissolved in 0.9% NaCl solution; a phospholipid derivative in water was added to form a water-soluble phospholipo-r-hGH-complex. This was then slowly added into the oil-phase as before.

The oil-phase consisted of egg yolk lecithin, cholesterol, glycerol-1-monooleate, d-alpha- tocopherol, an anti-oxidants solution and Tween-80. This 'water-in-oil' emulsion was passed through the microfluidizer-homogeniser once in the cold. Each ml of r-hGH microemulsion contains the following:

| Chemicals | mg/ml of r-hGH emulsion |
| --- | --- |
| Lecithin, egg yolk | 37.50 |
| L-alpha-phosphatidic acid bimyristoyl | 0.095 |
| 1,2,dimyristoyl-sn-glycerol-3-phosphocholine monohydrate | 1.91 |
| Cholesterol | 30.48 |
| Glycerol-monooleate | 27.81 |
| Oleic acid | 242.30 |
| Tween-80 | 17.91 |
| Water | 119.05 |

The pH was adjusted to 7.2 with 10 mm sodium phosphate buffer.

(Note that the trypsin-inhibitor aprotinin was not added in this example.)

EXAMPLE 5

In this example, salmon calcitonin (supplied by the Rorer Central Research of Hirsham, Pa., USA; NPD #8906046 NPP #211) was bound with egg yolk lecithin in the presence of aprotinin in 0.9% saline solution; the pH was adjusted to 2.0 with citric acid and ascorbic acid. In this way, a 'water-soluble' phospholipid-sCT-aprotinin complex was formed and this was made into a water-in-oil microemulsion as described in Example 1 above. Each portion of the formulation containing 100 IU of sCT contained the following:

| Chemicals | mg/100 IU of sCT |
| --- | --- |
| Egg yolk lecithin | 13.016 |
| Aprotinin | 1500 IU |
| sCT | 100 IU |
| Polyoxy-40-stearate | 2.646 |
| Hydroxypropylcellulose-SL | 5.026 |
| Sodium Benzoate | 1.587 |
| Citric acid | 1.720 |
| Ascorbic acid | 1.244 |
| Cholesterol | 10.582 |
| d-alpha-tocopherol | 0.265 |
| Glycerolmonooleate | 9.418 |
| Oleic acid | 84.127 |

-continued

| Chemicals | mg/100 IU of sCT |
|---|---|
| Tween-80 | 6.217 |
| Propylparaban | 0.529 |
| Methylparaban | 1.852 |
| Sesame seed oil (chemical grade) | 2.646 |
| Anti-oxidants | 1.111 |
| Ethanol* | 41.336 |
| Deionised water | 66.137 |

(*Most of the ethanol is evaporated).

EXAMPLE 6

A powdery or granular form of the insulin preparation of Example 1 may be prepared by spray coating the above microemulsion onto a pharmacologically inert carrier base, such as carboxymethylcellulose-Ca, gelatin, hydroxypropylcellulose-L, alginic acid or a mixture of them. The powdery (or granular) insulin-containing preparation is packed into No. 1 size hard gelatin capsules to give the following composition:

| Chemicals | mg per Capsule (approximate) |
|---|---|
| Bovine insulin | @ 4.5 to 6.0 IU |
| Dimyristoyl glycerol phosphocholine* | 2.2 |
| Aprotinin | @ 0.14 KIU |
| Polyoxy-40-stearate | 1.2 |
| Cholesterol | 5.2 |
| Oleic acid | 42.0 |
| Glycerolmonooleate | 4.8 |
| Tween-80 | 3.1 |
| Vitamin-E | 0.55 |
| Carboxymethylcellulose-Ca | 90.9† |
| Alginic acid | 45.5† |
| Gelatin | 22.7† |
| Hydroxypropylcellulose-L | 25.2† |

Each No. 1 Size Hard gelatinous capsule to weigh 250 mg.
*1,2-dimyristoyl-sn-glycerol-3-phosphocholine monohydrate
†These are practically non-absorbable in men and are thus pharmacologically inert, inactive materials.

BIOLOGICAL EXAMPLE A

Using an oral drug delivery system prepared as described in Example 1 (lecithin-bovine insulin-aprotinin), a clinical study was conducted in a group of known diabetics. The formulation of Example 1 was found to be effective in lowering systemic blood sugar as follows:

It was interesting to note that, in general, the onset of the hypoglycaemic effect of the lecithin-bovine insulin formulation after its oral administration was rather fast, occurring between 30 to 90 minutes after medication; blood sugar levels were slightly elevated at 120 minutes or so after the oral dosing of insulin in this formulation, and were lowered again after 3 hours or more: this oral formulation of insulin therefore has a dual phasic effect. By binding the lipophilic regions of bovine insulin with phospholipids, such as lecithin, a phospholipo-insulin complex (which then becomes a hydrophilic compound like other lipoproteins are in human body) is formed. Part of the phospholipo-insulin complex appears to cause an immediate hypoglycaemic reaction by its immediate absorption from the human gastrointestinal system; the rest of it (, that is, that part which did not react with peripheral insulin-receptors) appears to be directed into the liver, stored temporarily in the liver, and then released into the circulating blood causing the second reaction at the insulin receptors.

BIOLOGICAL EXAMPLE B

Eight healthy, normal male volunteers participated in this study. After overnight fasting, on Study Day 1 the subjects received medication as follows:

| Subject | Study Medication-EPO dose (IU) | |
|---|---|---|
| A | EPO intravenous infusion | 10 IU/Kg |
| B | ODDS-EPO, per os | 20 IU/Kg |
| C | Placebo, per os | 0 IU/Kg |
| D | EPO intravenous infusion | 10 IU/Kg |
| E | ODDS-EPO, per os | 15 IU/Kg |
| F | Placebo, per os | 0 IU/Kg |
| G | ODDS-EPO, per os | 20 IU/Kg |
| H | ODDS-EPO, per os | 15 IU/Kg |

Blood samples were collected at time 0, 0.5, 1, 2, 3, 4, 6, 10 and 14 hours after the medication; reticulocyte counts (%) were made and plasma EPO levels were measured by radioimmunoassay.

On Day 2 and Day 3, each subject was given the assigned coded study medications at 08:00 a.m., 14:00 p.m. and 22:00 p.m. and, after an overnight fast, on Study Day 4, each subject was examined again after having been given the study medications as above.

Reticulocyte counts, especially, on Study Day 4, were increased after 20 IU/kg and after 15 IU/kg of oral EPO as well as after 10 IU/Kg EPO intravenous infusion in these normal volunteers. The reticulocyte counts gradually decreased in the placebo group.

| Patient | | | | Blood Sugar (mg %) | | | | | | | |
|---|---|---|---|---|---|---|---|---|---|---|---|
| Code | Sex | Age | Wt* | 0** | 30 | 60 | 90 | 120 | 180 | 240 | Type |
| A | F | 45 | 55 | 257 | 190 | 169 | — | 214 | 138 | 89 | NIDDM |
| B | M | 50 | 42 | 155 | 110 | 108 | — | 132 | 149 | 128 | IDDM |
| C | M | 60 | 68 | 175 | 149 | 143 | — | 160 | 151 | 130 | NIDDM |
| D | F | 40 | 56 | 184 | — | — | 130 | — | 173 | — | IDDM |
| E | M | 66 | 61 | 169 | — | 141 | — | 104 | — | — | NIDDM |
| F | F | 53 | 65 | 316 | — | 206 | — | 184 | — | — | NIDDM |
| G | F | 49 | 45 | 320 | — | 275 | — | 296 | — | — | IDDM |
| H | F | 57 | 67 | 169 | — | 167 | — | 121 | — | — | NIDDM |
| J | M | 43 | 70 | 186 | — | 173 | — | 137 | — | — | IDDM |
| K | M | 69 | 66 | 195 | — | — | 136 | — | 154 | — | NIDDM |

*Wt = Body weight (Kg);
**0 = 0-Minute

On Study Day 1, plasma RIA-measured EPO levels were markedly increased after both 20 IU/kg and 15 IU/kg oral EPO as well as after 10 IU/kg EPO, intravenous infusion. With the placebo group, once again the EPO levels gradually decreased over the study period. EPO delivered by the formulation of Example 2 was orally effective and bioavailable in men.

BIOLOGICAL EXAMPLE C

The formulation prepared in Example 3 (a dimyristoylglycerol-phosphocholine-phosphatidic bimyristoyl-pSCT complex), was intraduodenally infused into a group of conscious pigs. Serial blood sugar levels and plasma pST levels (measured by radioimmunoassay) were assayed before and after the administration of the formulation of Example 3. The results, below, show a correlative rise in blood sugar and an increase in RIA-measured pST levels.

Blood Glucose (CHO) and Plasma pST levels (RIA) after Intra-Duodenal Infusion of Oral pST in Pigs

| Time (hr) | Pig-1 pST = 0 | | Pig-2 pST = 40 ml | | Pig-3 pST = 20 ml | |
|---|---|---|---|---|---|---|
| | CHO* | RIA** | CHO | RIA | CHO | RIA |
| −1 | <2 | <0.50 | <2 | 1.86 | 2.2 | 1.51 |
| 0 | 2.7 | 1.82 | <2 | 0.71 | <2 | 1.17 |
| 1 | 2.5 | 1.75 | 2.2 | 2.48 | 2.2 | 0.98 |
| 2 | 2.6 | 1.30 | 3.7 | 0.59 | 5.9 | 8.63 |
| 4 | 2.2 | 0.65 | 3.2 | 3.18 | 3.4 | 2.72 |
| 5 | 2.5 | 1.64 | 2.9 | 2.14 | 2.2 | 0.77 |
| 6 | 2.4 | 1.30 | 3.3 | 2.30 | 3.2 | 1.29 |
| 8 | <2 | <0.50 | 2.6 | 0.9 | 3.4 | 4.81 |
| 10 | 3.9 | — | 3.1 | 2.61 | 4.8 | 1.07 |
| 12 | 2.2 | — | <2 | 0.85 | 2.9 | 1.06 |
| 14 | 2.9 | — | 2.5 | 2.39 | 2.5 | 4.03 |
| 24 | — | — | — | 0.71 | — | 4.29 |

Blood Sugar and Plasma pST Levels after Intraduodenal Infusion of Oral pST

| Time (hr) | Pig-4 pST = 10 | | Pig-5 pST = 5 ml | | Pig-6 pST = 5 ml | |
|---|---|---|---|---|---|---|
| | CHO | RIA | CHO | RIA | CHO | RIA |
| −1 | 5.65 | 1.63 | 5.2 | 2.67 | 4 | 1.32 |
| 0 | 6.95 | 2.97 | 6.5 | 1.07 | 5.8 | 1.01 |
| 1 | 5.8 | 0.89 | 5.3 | 0.49 | 5.5 | 3.85 |
| 2 | 5.5 | 0.38 | 5.15 | 1.1 | 5.2 | 2.64 |
| 3 | 4.5 | — | 4.85 | — | 3.55 | — |
| 4 | 4.7 | 6.64 | 5.3 | 1.44 | 5.0 | 1.1 |
| 5 | 5.1 | 1.67 | 5.35 | 1.10 | 5.5 | 1.2 |
| 6 | 5.65 | 1.47 | 5.25 | 0.7 | 5.8 | 3.56 |
| 8 | 5.34 | 0.85 | 5.15 | 1.71 | 5.35 | 2.48 |
| 10 | 7.05 | 5.99 | 6.8 | 1.80 | 6.6 | 2.04 |
| 12 | 6.25 | 3.54 | 5.3 | 0.79 | 7.05 | 2.49 |
| 14 | 7.55 | 0.82 | 7.05 | 2.14 | 8.25 | 1.11 |
| 24 | 6.75 | 0.84 | 6.1 | 0.91 | 7.15 | 3.49 |
| 36 | 7.35 | 0.93 | 8.45 | 1.45 | 8.9 | 1.06 |

*CHO = Blood Glucose Levels (mMol/l)
**RIA = RIA measured plasma pST levels (ng/ml)

BIOLOGICAL EXAMPLE D

Using the formulation prepared in Example 4 (which involves a phospholipid-r-human growth hormone complex), the clinical bioactivity (measured as changes induced by oral r-hGH on blood sugar levels) and bioavailability of orally-administered r-hGH were studied in nine young, healthy male volunteers.

TABLE

Topography of Study Subjects (all male subjects)

| Name | Age | Height (cm) | Weight (kg) | Oral r-hGH Dose (mg) |
|---|---|---|---|---|
| JBL | 26 | 172 | 66 | 7 |
| PJG | 22 | 179 | 68 | 7 |
| NMH | 20 | 178 | 60 | 15 |
| CSB | 24 | 175 | 65 | 15 |
| KKN | 22 | 172 | 57 | 30 |
| CSK | 20 | 172 | 57 | 30 |
| CYG | 25 | 174 | 60 | PLACEBO |
| KJH | 27 | 175 | 65 | PLACEBO |
| YKS | 20 | 175 | 60 | PLACEBO |

Figure 10:
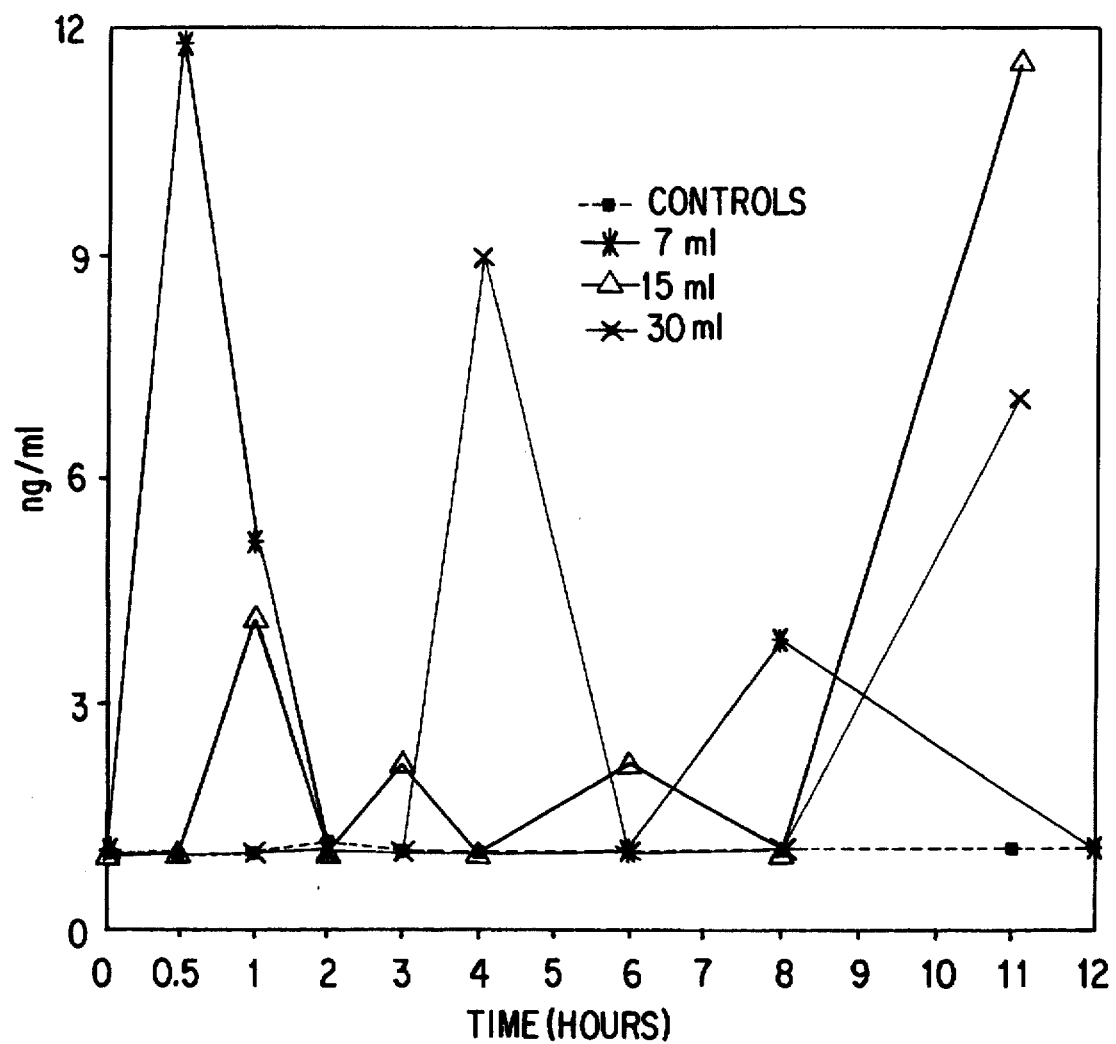
FIG. 10 shows the average dose-responsiveness of the subjects to the oral administration.

Changes in blood sugar and hGH levels induced by oral administration of oral r-hGH in these 9 subjects at doses of 0, 7, 15, and 30 ml (0, 7, 15, and 30 mg of oral r-hGH formulation) were measured. Measurements were made by commercial kits on EDTA-treated plasma. Results for each subject are illustrated individually in FIGS. 1 to 9 and the average dose-responsiveness to the oral administration of r-hGH on RIA-measured plasma hGH is illustrated in FIG. 10. A 'diabetogenicity' effect and an RIA-measurable elevation in plasma hGH were observed and, in all volunteers treated with active drug, such changes were 'biphasic' as has been observed with the administration of other formulations in accordance with this invention, such as oral pST in pigs and oral insulin in diabetics.

Once again, apparently, the r-hGH administered orally (as phospholipo-r-hGH) is absorbed and induces the biological actions of hGH in humans. It is bioavailable in circulating blood usually at between 0.5 to 4 hours after oral dosing; the hGH is believed to be channelled into the liver, from where it is released and available at the circulating blood once again after some 8 to 12 (or more) hours from oral dosing. This biphasic effect in hGH bioavailability (and additionally in bioactivity) is apparently dose-dependent: at relatively lower doses, oral hGH was bioavailable within 0.5 to 2 hours after oral dosing, and once again bioavailable after 8 hours or so; whereas at higher dose (30 mg of r-hGH), the initial peak bioavailability occurred at about 4 hours and the second peak was observed after 11 hours from the oral dose.

A recommended possible dose was 15 mg per man. In our study, 7 mg was also a significantly effective dose. 1 to 10 mg per man, in particular 3–5 mg per man may be a suitable therapeutic dose.

BIOLOGICAL EXAMPLE E

The formulation of Example 5 (oral delivery form of salmon calcitonin: ODDS-sct) was studied in a group of young male volunteers. The demography of these volunteers is as follows:

| Subject Code | Age (years) | Weight (kg) | Height (cm) | Blood Pressure (mmHg) Systolic/Diastolic | Pulse Rate beats/min |
|---|---|---|---|---|---|
| A | (10)* 23 | 78 | 187 | 120/80 | 72 |
| B | (5)* 23 | 73 | 183 | 140/100 | 56 |
| C | (100) +20 | 59 | 172 | 110/70 | 56 |
| D | (10)* 25 | 61 | 173 | 100/60 | 60 |
| E | (100) +25 | 66 | 169 | 120/80 | 64 |
| F | (5)* 23 | 63 | 174 | 100/60 | 60 |

(*Number of ODDS-sCT capsules, each capsule containing 60 IU)
(+IU of salmon calcitonin injected, subcutaneously)

Briefly, each subject was fasted over-night and either the ODDS-sCT capsules were administered, per os, or CALSY- NAR™ (an injectable salmon calcitonin preparation) was administered subcutaneously at 6:00 a.m. of the study day. Venous blood samples were collected through an indwelling catheter in a forearm vein at time 0, 60, 90, 120, 150, 180, 210, 240, 300, and 360 minutes after the administration of testing medication. Serum phosphate levels were measured, immediately after collecting the blood samples, while plasma salmon calcitonin levels were measured by radio-immunoassay on EDTA-treated plasma samples.

A marked reduction in serum phosphate levels was observed in all subjects who had received either 300 IU or 600 IU of ODDS-sCT capsules, and such changes in serum phosphate levels after oral administration of the salmon calcitonin formulation of Example 5 were similar to those of subjects after subcutaneous injection of salmon calcitonin. 300 IU and 600 IU of orally aministered ODDS-sCT are thus shown to have a broadly similar effect on serum phosphate level 100 IU of s.c. injected sCT. Formulations of the present invention are therefore highly effective.

EXAMPLE 7

A phospholipo-salmon calcitonin complex was made by mixing 1,2-dimyristoyl-sn-glycerol-3-phosphatidic acid monohydrate, and L-α-phosphatidiycholine bimyristoyl (sodium salt) in the presence of aprotinin in 0.9% of isotonic saline solution, and a chemical 'interaction' was induced at room temperature for 30 minutes. The phospholipids, which are known to participate in the L-α-phosphatidylglycerol pathway of synthesis of phosphotidylcholine at the epithelium of the small intestine, apparently non-covalently bind at the lipophilic sites of salmon calcitonin, in vitro.

The above phospholipo-salmon calcitonin complex is suspended and mixed with a solution containing a surfactant having an HLB value of 14 or more (polyoxy-40-stearate) in the presence of a viscosity increaser (thickener) and 'stabiliser' for the suspended phospholipocalcitonin (eg, less than 5%, preferably less than 2% of hydroxypropylcellulose). The pH was adjusted to around pH 2.0 or so using concentrated solutions of citric acid and ascorbic acid (although any other acidic pH adjuster(s) could be used).

The solution yielded above is suspended into three to four volumes of oleic acid (or any other $C_{16}$ or higher fatty acid) in the presence of a surfactant having an HLB value of 4 or less. The $C_{16}$ or higher fatty acid(s) may act as a "volume expander", as well as possibly an enhancer for transmembrane absorption of the phospholipo-salmon calcitonin, and/ or as an "enteric coating" for the phospholipo-salmon calcitonin. However, this oleic acid/surfactant combination is not absolutely essential.

The following shows the actual chemical composition of the phospholipo-salmon calcitonin preparation of this example:

| Chemical Ingredients | Weight (mg or gm) | | Remarks |
|---|---|---|---|
| | Preferred | Optimal | |
| Part A: | | | |
| Salmon calcitonin | 200–1500 mg | 480 mg | Rorer* |
| 1,2-dimyristoyl-sn-glycerol-3-phosphotidic acid monohydrate | 50–1000 mg | 500 mg | |
| L-alpha-phosphocholine bimyristoyl (sodium salt) | 50–1000 mg | 500 mg | |
| Aprotinin | 250–50000 mg | 10 gm | (12 TIU. mg) |
| Isotonic saline solution | 50–400 mg | 150 gm | |
| Part B: | | | |
| Hydroxypropylcellulose | 500–7200 mg | 1.5 gm | |
| Polyoxy-40-stearate | 2–12 gm | 4 gm | |
| Citric acid | 1–5 gm | 2.4 gm | |
| Ascorbic acid | 1–7 gm | 3.0 gm | |
| Part C: | | | |
| Oleic acid | 125–1200 gm | 540 gm | |
| Tween-80 | 5–42 gm | 10.5 gm | |
| Glycerolmonooleate | 7.3–124.2 gm | 41.4 gm | |

(*Rorer salmon calcitonin, Lot # NPP 209; 8908047)

The procedure of making the formulation was as follows:

Part A was thoroughly mixed and left to stand at room temperature for 30 minutes or more. Part B was mixed and prepared and then Part A was suspended in Part B under gentle stirring at room temperature. The pH was adjusted with citric acid and ascorbic acid to about pH 2.0.

Part C, the oil solution, was prepared by mixing. With gentle stirring, the Part A and Part B prepartion was poured into Part C.

This mixed solution may be spray coated over approximately the same weight of powder consisting either of carboxymethyl-cellulose-Ca and alginic acid or of alginic acid and gelatin. The coated dried powder may be packed into a hard gelatin capsules and may be orally administered to human subjects/patients. Alternatively, the liquid form may be orally administered either in a soft gelatin capsule or by itself.

BIOLOGICAL EXAMPLE F

Six young healthy male volunteers participated in this study. After an overnight fasting, at 05:30 am the Example 7 salmon calcitonin preparation was orally administered to four subjects: two subjects received 300 IU of salmon calcitonin capsule as in Example 7, and another two subjects received 600 IU of oral salmon calcitonin as in Example 7. Two subjects were given CALCYNAR, a trade mark for an injectable salmon calcitonin, 100 IU, subcutaneously. Serum phosphate and plasma calcitonin levels, measured by means of radioimmunoassay method, were taken at 30 minutes before medication, at the time of medication, and at 30, 60, 90, 120, 150, 180, 210, 240 and 300 minutes after medication.

TABLE

Changes in serum phosphate (% of the control) and RIA-measured plasma sCT (P g/ml) in men after oral salmon calcitonin (Example 7 formulation) and after subcutaneous injection of CALCYNAR:

| Time(min) | RIA-sCT (P g/ml) | | | | | | Serum Phosphate (-% Change) | | | | | |
|---|---|---|---|---|---|---|---|---|---|---|---|---|
| Subj.* | A | B | C | D | E | F | A | B | C | D | E | F |
| 0 | N | N | 105 | N | N | N | 4.54 | 4.01 | 4.31 | 4.50 | 4.88 | 5.11++ |
| 30 | N | N | 150 | N | 220 | 34 | 7.1 | 5.7 | 12.5 | 14.2 | 9.4 | 2.5 |
| 60 | N | N | 100 | N | 100 | 94 | 10.6 | 17.2 | 15.8 | 20.7 | 1.8 | 7.2 |
| 90 | 48 | N | 44 | N | 48 | 62 | 17.8 | 21.2 | 17.2 | 25.8 | 6.6 | 11.0 |
| 120 | 116 | N | 19 | N | 40 | 70 | 22.0 | 36.2 | 17.0 | 28.4 | 9.2 | 8.2 |
| 150 | 138 | N | 42 | N | 16 | 63 | 17.4 | 16.0 | 13.0 | 2.7 | +7.0 | 3.3 |
| 180 | 50 | N | N | N | 48 | 120 | 30.8 | 31.9 | 29.2 | 36.4 | 18.4 | 15.1 |
| 210 | N | N | N | N | N | 70 | 30.4 | 30.9 | 35.0 | 32.4 | 16.2 | 19.2 |
| 240 | N | N | N | N | N | 60 | 24.9 | 29.2 | 31.3 | 20.7 | 17.0 | 13.5 |
| 300 | N | N | N | N | 20 | 56 | 18.4 | 28.2 | 27.2 | 27.8 | 19.7 | 17.03 |
| 360 | N | N | N | N | 24 | 48 | 11.0 | 12.0 | 23.9 | 18.2 | 26.6 | 8.6 |

*Subj = Subject
++5.11 (at Time 0 Minute) = Serum phosphate level at the control, baseline value in mg/ml serum.
Note:
All % changes in the serum phosphate levels are in (−) "minus" values, except where indicated. (The + sign means an increase in serum phosphate level).

Code for Study Medication Dosings:

Subject A=600 IU oral sCT as the Example I formulation, per os;
Subject B=300 IU, per os;
Subject C=100 IU CALCYNAR; subcutaneous injection;
Subject D=600 IU, per os;
Subject E=100 IU, CALCYNAR, subcutaneous injection;
Subject F=300 IU, per os.

The Example 7 formulation of salmon calcitonin given orally to a group of healthy male subjects was biologically active in reducing serum phosphate to an extent which was equal to or greater than that effect of subcutaneously injected salmon calcitonin in men. However, RIA-measurable plasma sCT was not always detectable by the present methodology applied after oral ingestion of either 600 or 300 IU of Example 7 salmon calcitonin. By binding sCT with phospholipids, certain antigenic changes in the sCT may be caused; the sCT may therfore not be detected by currently the sCT-specific antibodies used in the radioimmunoassay.

EXAMPLE 8

An orally administrable insulin (bovine insulin) preparation was made by mixing insulin with L-α-phosphocholine (lecithin precursor) in the presence of an appropriate surfactant and aprotinin in isobutyl alcohol (0.9%). The noncovalently bound complex thus formed was suspended into water and MCT (medium chain-length triglycerides) oil for subsequent oral administration to a group of diabetics.

The following is the chemical composition of the formulation:

| | Weight (mg or gm) | |
|---|---|---|
| Chemical Ingredients | Preferred | Optimal |
| Part A: | | |
| Bovine insulin | 0.5–5 gm | 1 gm |
| L-alpha-phosphocholine | 50–2000 mg | 500 mg |

-continued

| | Weight (mg or gm) | |
|---|---|---|
| Chemical Ingredients | Preferred | Optimal |
| Aprotinin as TRASYLOL™ (5 ml = 100,000 KIU) | 50–250 ml | 150 ml |
| Citric acid | 1–5 gm | 2.4 gm |
| Ascorbic acid | 1–7 gm | 3.0 gm |
| Part B: | | |
| Polyoxy-40-stearate | 2–12 gm | 4.0 gm |
| Hydroxypropylcellulose | 0.5–8 gm | 1.5 gm |

The formulation was prepared as follows:

Part A was mixed at room temperature thoroughly with gentle stirring. Part B was prepared by dissolving HPC and polyoxy-40-stearate completely in 100 ml of deionized water. Part A was then added to Part B, with gentle stirring and thorough mixing at room temperature.

This insulin formulation may be given orally to diabetics as it is, or it may be suspended into 10 to 30 ml of MCT (medium chain-length triglyceride) oil, which may act as an enteric coating and a volume expander, so as to promote gastric emptying of the formulation through the pylorus and into duodeno-jejuno-ileum.

BIOLOGICAL EXAMPLE G

Eight diabetic patients participated in this study. While fasting, early in the morning of the study, each subject took orally the Example 8 oral insulin formulation; the blood sugar was measured for two hours.

| | | | | | Dose | Blood Sugar (mMol/dl) | | |
|---|---|---|---|---|---|---|---|---|
| Name | Sex | Age | Wt(Kg) | Type | (IU) | 0 | 60 | 120(Min) |
| COJ | F | 77 | 60 | II | 30 | 10.4 | — | 9.4 |
| KDS | M | 63 | 63 | II | 24 | 9.3 | 8.5 | 8.1 |
| SDG | M | 51 | 52 | II | 24 | 10.4 | 8.4 | 7.0 |
| HKH | M | 44 | 70 | I | 24 | 9.5 | 7.9 | 7.8 |
| CYH | M | 39 | 50 | I | 24 | 9.1 | 7.8 | — |

-continued

| Name | Sex | Age | Wt(Kg) | Type | Dose (IU) | Blood Sugar (mMol/dl) 0 | 60 | 120(Min) |
|---|---|---|---|---|---|---|---|---|
| NCS | F | 53 | 65 | II | 30 | 14.5 | 10.8 | 10.1 |
| SKW | M | 66 | 61 | II | 30 | 10.5 | 9.7 | 8.7 |
| YYC | F | 49 | 57 | II | 48 | 20.2 | 17.3 | 13.7 |

The insulin formulation of Example 8, when orally administered, was effective in controlling hyperglycemia of both diabetic types.

We claim:

1. A water-in-oil pharmaceutical formulation for oral or rectal administration comprising a hydrophilic phase dispersed in a lipophilic phase to form an emulsion, wherein said hydrophilic phase comprises (a) water, (b) a biologically active material and (c) in association with the biologically active material, lecithin or a lecithin precursor, wherein said lipophilic phase comprises (a) one or more oils, (b) a phospholipid and (c) a lipophilic surfactant, and wherein an emulsion is formed from said hydrophilic phase dispersed in said lipophilic phase.

2. The formulation as claimed in claim 1, wherein said biologically active material comprises a protein.

3. The formulation as claimed in claim 2, wherein said protein is insulin, erythropoietin, porcine somatotropin, human growth hormone or calcitonin.

4. The formulation as claimed in claim 1, wherein said lecithin precursor is a phospholipid.

5. The formulation as claimed in claim 4, wherein said phospholipid has the general formula:

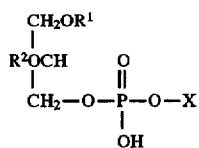

and wherein each of R1 and R2 independently represents an acyl group and X represents a hydrogen atom or a phospholipid headgroup.

6. The formulation as claimed in claim 5, wherein said phospholipid headgroup contains a residue of ethanolamine, choline, serine or glycerol.

7. The formulation as claimed in claim 6, wherein said phospholipid comprises:
dimyristoryl phosphatidyl glycerol (DMPG);
dipalmitoyl phosphatidyl glycerol (DPPG);
distearoyl phosphatidyl glycerol (DSPG);
dimyristoyl phosphatidylcholine (DMPC);
dipalmitoyl phosphatidylcholine (DPPC);
distearoyl phosphatidylcholine (DSPC);
dimyristoyl phosphatidic acid (DMPA);
dipalmitoyl phosphatidic acid (DPPA); or
distearoyl phosphatidic acid (DSPA).

8. The formulation as claimed in claim 6, wherein said phospholipid comprises:
dimyristoyl phosphatidyl ethanolamine (DMPE);
dipalmitoyl phosphatidyl ethanolamine (DPPE); or
distearoyl phosphatidyl ethanolamine (DSPE).

9. The formulation as claimed in claim 1, comprising a lecithin.

10. The formulation as claimed in claim 1, comprising a hydrophilic liquid.

11. The formulation as claimed in claim 1, wherein said hydrophilic phase further comprises a hydrophilic surfactant.

12. The formulation as claimed in claim 1, further comprising a protease inhibitor.

13. The formulation as claimed in claim 1, further comprising a stabilizer for the biologically active material.

14. The formulation as claimed in claim 1, further comprising an emulsification aid.

15. The formulation as claimed in claim 1, further comprising a stabilizer or a plasticizer or both.

16. The formulation as claimed in claim 1, further comprising a preservative.

17. The formulation as claimed in claim 16, wherein said preservative comprises an antioxidant.

18. The formulation as claimed in claim 1, wherein said formulation is coated on a solid core.

19. A method for the treatment or prophylaxis of a human or other animal with a disorder treatable or controllable by a normally parenterally administered biologically active material comprising the oral or rectal administration of a formulation as claimed in claim 1.

20. A water-in-oil pharmaceutical formulation for oral or rectal administration comprising a hydrophilic phase dispersed in a lipophilic phase to form an emulsion, wherein said hydrophilic phase comprises (a) water, (b) a biologically active material and (c) in association with the biologically active material lecithin or a lecithin precursor, wherein said lipophilic phase comprises (a) materials that can be used to form a chylomicron matrix, (b) a phospholipid and (c) a lipophilic surfactant, and wherein an emulsion is formed from said hydrophilic phase dispersed in said lipophilic phase.

21. The formulation as claimed in claim 20, wherein said chylomicron matrix comprises cholesterol or cholesterol ester, or both.

22. The formulation as claimed in claim 21, wherein said phospholipid is lecithin.

23. The formulation as claimed in claim 20, wherein said biologically active material is insulin, erythropoietin, porcine somatotropin, human growth hormone or calcitonin.

24. The formulation as claimed in claim 20, wherein said lecithin precursor is a phospholipid.

25. The formulation as claimed in claim 24, wherein said phospholipid has the general formula:

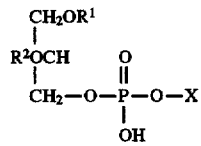

wherein each of R1 and R2 independently represents an acyl group and X represents a hydrogen atom or a phospholipid headgroup.

26. The formulation as claimed in claim 25, wherein said phospholipid headgroup contains a residue of ethanolamine, choline, serine or glycerol.

27. The formulation as claimed in claim 26, wherein said phospholipid comprises:
dimyristoyl phosphatidyl glycerol (DMPG);
dipalmitoyl phosphatidyl glycerol (DPPG);
distearoyl phosphatidyl glycerol (DSPG);

dimyristoyl phosphatidylcholine (DMPC);
dipalmitoyl phosphatidylcholine (DPPC);
distearoyl phosphatidylcholine (DSPC);
dimyristoyl phosphatidic acid (DMPA);
dipalmitoyl phosphatidic acid (DPPA); or
distearoyl phosphatidic acid (DSPA).

28. The formulation as claimed in claim 26, wherein said phospholipid comprises:
dimyristoyl phosphatidyl ethanolamine (DMPE);
dipalmitoyl phosphatidyl ethanolamine (DPPE); or
distearoyl phosphatidyl ethanolamine (DSPE).

29. The formulation as claimed in claim 20, comprising a lecithin.

30. The formulation as claimed in claim 20, comprising a hydrophilic liquid.

31. The formulation as claimed in claim 20, wherein said hydrophilic phase further comprises a hydrophilic surfactant.

32. The formulation as claimed in claim 20, further comprising a protease inhibitor.

33. The formulation as claimed in claim 20, further comprising a stabilizer for the biologically active material.

34. The formulation as claimed in claim 20, further comprising an emulsification aid.

35. The formulation as claimed in claim 20, further comprising a stabilizer or a plasticizer or both.

36. The formulation as claimed in claim 20, further comprising a preservative.

37. The formulation as claimed in claim 36, wherein said preservative comprises an antioxidant.

38. The formulation as claimed in claim 20, wherein said formulation is coated on a solid core.

39. A method for the treatment or prophylaxis of a human or other animal with a disorder treatable or controllable by a normally parenterally administered biologically active material comprising the oral or rectal administration of a formulation as claimed in claim 20.

40. A water-in-oil pharmaceutical formulation for oral or rectal administration comprising a hydrophilic phase dispersed in a lipophilic phase to form an emulsion,
wherein said hydrophilic phase comprises (a) water, (b) a biologically active material and (c) in association with the biologically active material, lecithin or a lecithin precursor comprising a phospholipid,
wherein said lipophilic phase comprises (a) one or more oils, (b) a phospholipid and (c) a lipophilic surfactant, and wherein an emulsion is formed from said hydrophilic phase dispersed in said lipophilic phase.

41. A water-in-oil pharmaceutical formulation for oral or rectal administration comprising a hydrophilic phase dispersed in a lipophilic phase to form an emulsion,
wherein said hydrophilic phase comprises (a) water, (b) a biologically active material and (c) in association with the biologically active material, a phospholipid, wherein said phospholipid has the general formula:

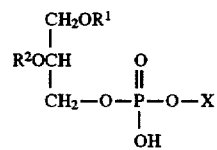

and wherein each of R1 and R2 independently represents an acyl group and X represents a hydrogen atom or a phospholipid headgroup,
wherein said lipophilic phase comprises (a) one or more oils, (b) a phospholipid and (c) a lipophilic surfactant, and wherein an emulsion is formed from said hydrophilic phase dispersed in said lipophilic phase.

42. The formulation as claimed in claim 40 or 41, wherein said biologically active material comprises a protein.

43. The formulation as claimed in claim 42, wherein said protein is insulin, erythropoietin, porcine somatotropin, human growth hormone or calcitonin.

44. The formulation as claimed in claim 40 or 41, wherein said phospholipid headgroup contains a residue of ethanolamine, choline, serine or glycerol.

45. The formulation as claimed in claim 40 or 41, wherein said phospholipid comprises:
dimyristoryl phosphatidyl glycerol (DMPG);
dipalmitoyl phosphatidyl glycerol (DPPG);
distearoyl phosphatidyl glycerol (DSPG);
dimyristoyl phosphatidylcholine (DMPC);
dipalmitoyl phosphatidylcholine (DPPC);
distearoyl phosphatidylcholine (DSPC);
dimyristoyl phosphatidic acid (DMPA);
dipalmitoyl phosphatidic acid (DPPA); or
distearoyl phosphatidic acid (DSPA).

46. The formulation as claimed in claim 40 or 41, wherein said phospholipid comprises:
dimyristoyl phosphatidyl ethanolamine (DMPE);
dipalmitoyl phosphatidyl ethanolamine (DPPE); or
distearoyl phosphatidyl ethanolamine (DSPE).

* * * * *